§ 371 (c)(1),
(2) Date: Feb. 26, 2018

(87) PCT Pub. No.: WO2017/033363

PCT Pub. Date: Mar. 2, 2017

(65) Prior Publication Data

US 2018/0243898 A1 Aug. 30, 2018

(30) Foreign Application Priority Data

Aug. 25, 2015 (JP) .................................. 2015-165479

(51) Int. Cl.
G05B 19/04 (2006.01)
G05B 19/18 (2006.01)
(Continued)

(12) United States Patent
Hashimoto et al.

(10) Patent No.: US 10,631,941 B2
(45) Date of Patent: Apr. 28, 2020

(54) ROBOT SYSTEM

(71) Applicant: KAWASAKI JUKOGYO KABUSHIKI KAISHA, Kobe-shi, Hyogo (JP)

(72) Inventors: Yasuhiko Hashimoto, Kobe (JP); Nobuyasu Shimomura, Kobe (JP); Tsuyoshi Maehara, Itami (JP); Masayuki Kamon, Akashi (JP); Yasushi Kurosawa, Kakogawa (JP); Shigetsugu Tanaka, Akashi (JP)

(73) Assignee: KAWASAKI JUKOGYO KABUSHIKI KAISHA, Kobe (JP)

( * ) Notice: Subject to any disclaimer, the term of this patent is extended or adjusted under 35 U.S.C. 154(b) by 307 days.

(21) Appl. No.: 15/755,384

(22) PCT Filed: May 27, 2016

(86) PCT No.: PCT/JP2016/002590

(52) U.S. Cl.
CPC .............. *A61B 34/37* (2016.02); *A61B 34/32* (2016.02); *B23P 19/04* (2013.01); *B23Q 15/12* (2013.01);
(Continued)

(58) Field of Classification Search
CPC ......... A61B 34/32; A61B 34/37; B23P 19/04; B23P 21/00; B23P 21/002; B23Q 15/12;
(Continued)

(56) References Cited

U.S. PATENT DOCUMENTS 6,645,196 B1* 11/2003 Nixon .................... B25J 9/1664
128/898
2010/0268386 A1* 10/2010 Kiyota ................... G05B 19/42
700/264
(Continued)

FOREIGN PATENT DOCUMENTS

JP   S62-49403 A    3/1987
JP   S63-283878 A   11/1988
(Continued)

OTHER PUBLICATIONS

Aug. 16, 2016 International Search Report issued in International Patent Application No. PCT/JP2016/002590.
(Continued)

*Primary Examiner* — Harry Y Oh
(74) *Attorney, Agent, or Firm* — Oliff PLC

(57) ABSTRACT

Robot system which includes a master device configured to receive an operating instruction from an operator, slave arm, storage device configured to store operating sequence information that defines processing carried out by slave arm, and control device configured to control operation of slave arm. Control device includes a receiver configured to receive an input signal, motion controller configured to determine whether operating mode of slave arm is to be automatic,
(Continued)

manual or correctable automatic mode and control operation of slave arm in determined operating mode, and continuation determinator configured to determine whether continuation of automatic mode is permitted. In a process at which slave arm is scheduled to operate in automatic mode, after motion controller suspends operation of slave arm in automatic mode at a given step of process, continuation determinator determines whether continuation of automatic mode is permitted based on input signal received by receiver when operation is suspended.

6 Claims, 12 Drawing Sheets

(51) Int. Cl.
| | |
|---|---|
| A61B 34/37 | (2016.01) |
| G05B 19/418 | (2006.01) |
| B23P 19/04 | (2006.01) |
| B25J 13/00 | (2006.01) |
| B25J 19/04 | (2006.01) |
| B25J 9/00 | (2006.01) |
| B25J 9/16 | (2006.01) |
| B25J 13/08 | (2006.01) |
| B25J 3/00 | (2006.01) |
| B25J 13/06 | (2006.01) |
| B25J 18/00 | (2006.01) |
| B25J 19/02 | (2006.01) |
| B25J 3/04 | (2006.01) |
| B23Q 15/12 | (2006.01) |
| B25J 13/02 | (2006.01) |
| B25J 11/00 | (2006.01) |
| G06F 3/01 | (2006.01) |
| H04N 5/232 | (2006.01) |
| H04N 7/18 | (2006.01) |
| A61B 34/32 | (2016.01) |
| G06T 7/62 | (2017.01) |
| G06T 7/70 | (2017.01) |
| B23P 21/00 | (2006.01) |

(52) U.S. Cl.
CPC . *B25J 3/00* (2013.01); *B25J 3/04* (2013.01); *B25J 9/0081* (2013.01); *B25J 9/0084* (2013.01); *B25J 9/0087* (2013.01); *B25J 9/161* (2013.01); *B25J 9/1602* (2013.01); *B25J 9/163* (2013.01); *B25J 9/1612* (2013.01); *B25J 9/1628* (2013.01); *B25J 9/1633* (2013.01); *B25J 9/1646* (2013.01); *B25J 9/1653* (2013.01); *B25J 9/1664* (2013.01); *B25J 9/1669* (2013.01); *B25J 9/1674* (2013.01); *B25J 9/1682* (2013.01); *B25J 9/1689* (2013.01); *B25J 9/1697* (2013.01); *B25J 11/008* (2013.01); *B25J 13/00* (2013.01); *B25J 13/003* (2013.01); *B25J 13/006* (2013.01); *B25J 13/02* (2013.01); *B25J 13/025* (2013.01); *B25J 13/06* (2013.01); *B25J 13/065* (2013.01); *B25J 13/08* (2013.01); *B25J 13/084* (2013.01); *B25J 13/085* (2013.01); *B25J 13/087* (2013.01); *B25J 13/088* (2013.01); *B25J 18/00* (2013.01); *B25J 19/023* (2013.01); *B25J 19/028* (2013.01); *B25J 19/04* (2013.01); *G05B 19/4182* (2013.01); *G06F 3/017* (2013.01); *G06T 7/62* (2017.01); *G06T 7/70* (2017.01); *H04N 5/23219* (2013.01); *H04N 7/181* (2013.01); *B23P 21/00* (2013.01); *B23P 21/002* (2013.01); *G05B 2219/33007* (2013.01); *G05B 2219/35464* (2013.01); *G05B 2219/37297* (2013.01); *G05B 2219/39004* (2013.01); *G05B 2219/39102* (2013.01); *G05B 2219/39439* (2013.01); *G05B 2219/39531* (2013.01); *G05B 2219/39533* (2013.01); *G05B 2219/40022* (2013.01); *G05B 2219/40134* (2013.01); *G05B 2219/40136* (2013.01); *G05B 2219/40139* (2013.01); *G05B 2219/40142* (2013.01); *G05B 2219/40143* (2013.01); *G05B 2219/40145* (2013.01); *G05B 2219/40146* (2013.01); *G05B 2219/40161* (2013.01); *G05B 2219/40162* (2013.01); *G05B 2219/40163* (2013.01); *G05B 2219/40169* (2013.01); *G05B 2219/40182* (2013.01); *G05B 2219/40183* (2013.01); *G05B 2219/40195* (2013.01); *G05B 2219/40387* (2013.01); *G05B 2219/40627* (2013.01); *Y10S 901/02* (2013.01); *Y10S 901/03* (2013.01); *Y10S 901/08* (2013.01); *Y10S 901/09* (2013.01); *Y10S 901/10* (2013.01); *Y10S 901/27* (2013.01); *Y10S 901/41* (2013.01); *Y10S 901/46* (2013.01); *Y10S 901/47* (2013.01)

(58) Field of Classification Search
CPC ........ B25J 11/008; B25J 13/00; B25J 13/003; B25J 13/006; B25J 13/02; B25J 13/025; B25J 13/06; B25J 13/065; B25J 13/08; B25J 13/084; B25J 13/085; B25J 13/087; B25J 13/088; B25J 18/00; B25J 19/023; B25J 19/028; B25J 19/04; B25J 3/00; B25J 3/04; B25J 9/0081; B25J 9/0084; B25J 9/0087; B25J 9/1602; B25J 9/161; B25J 9/1612; B25J 9/1628; B25J 9/163; B25J 9/1633; B25J 9/1646; B25J 9/1653; B25J 9/1664; B25J 9/1669; B25J 9/1674; B25J 9/1682; B25J 9/1689; B25J 9/1697; G05B 19/4182; G05B 2219/33007; G05B 2219/35464; G05B 2219/37297; G05B 2219/39004; G05B 2219/39102; G05B 2219/39439; G05B 2219/39531; G05B 2219/39533; G05B 2219/40022; G05B 2219/40134; G05B 2219/40136; G05B 2219/40139; G05B 2219/40142; G05B 2219/40143; G05B 2219/40145; G05B 2219/40146; G05B 2219/40161; G05B 2219/40162; G05B 2219/40163; G05B 2219/40169; G05B 2219/40182; G05B 2219/40183; G05B 2219/40195; G05B 2219/40387; G05B 2219/40627; G06F 3/017; G06T 7/62; G06T 7/70; H04N 5/23219; H04N 7/181; Y10S 901/02; Y10S 901/03; Y10S 901/08; Y10S 901/09; Y10S 901/10; Y10S 901/27; Y10S 901/41; Y10S 901/46; Y10S 901/47
See application file for complete search history.

(56) References Cited

U.S. PATENT DOCUMENTS

2011/0301733 A1* 12/2011 Yoshima ............ B23K 9/0216
                                                                    700/96
2012/0191245 A1*  7/2012 Fudaba ............... B25J 9/1633
                                                                    700/254

(56) References Cited

U.S. PATENT DOCUMENTS

2014/0160015 A1\*  6/2014  Ogawa .................. B25J 13/02
                                                              345/156
2014/0163730 A1   6/2014  Mian

FOREIGN PATENT DOCUMENTS

| JP | 2003-311661 A | 11/2003 |
| JP | 2005-138245 A | 6/2005 |
| JP | 3924495 B2 | 6/2007 |
| JP | 2011-093064 A | 5/2011 |

OTHER PUBLICATIONS

Jun. 6, 2017 Office Action issued in Taiwanese Patent Application No. 105126373.

\* cited by examiner

| PERFORMING ORDER | <1> | <2> | <3> | <4> | <5> |
|---|---|---|---|---|---|
| OPERATION MODE | AUTOMATIC | MANUAL | AUTOMATIC | MANUAL | AUTOMATIC |
| OPERATION OF SLAVE ARM | TAKE OUT WORKPIECE A → MOVE TO READY-TO-ASSEMBLE POS. → WAIT FOR OPERATION | ASSEMBLE WORKPIECE A ACCORDING TO OPERATOR INPUT | EVACUATE FROM ASSEMBLING COMPLETED POS. → TAKE OUT WORKPIECE B → MOVE TO READY-TO-ASSEMBLE POS. → WAIT FOR OPERATION | ASSEMBLE WORKPIECE B ACCORDING TO OPERATOR INPUT | EVACUATE FROM ASSEMBLING COMPLETED POS. → MOVE TO ALL WORK COMPETED POS. |
| OPERATION OF OPERATOR | | OPERATIONAL INPUT (OPERATION OF MASTER ARM) → NOTIFY ASSEMBLING WORK COMPLETION | | OPERATIONAL INPUT (OPERATION OF MASTER ARM) → NOTIFY ASSEMBLING WORK COMPLETION | |

FIG. 3

| PERFORMING ORDER | <1> | <2> | <3> | <4> |
|---|---|---|---|---|
| OPERATION MODE | MANUAL | AUTOMATIC | MANUAL | AUTOMATIC |
| OPERATION OF SLAVE ARM | GRIP WORKPIECE A ACCORDING TO OPERATOR INPUT | MOVE WORKPIECE A TO WORK YARD → WAIT FOR OPERATION | GRIP WORKPIECE B ACCORDING TO OPERATOR INPUT | MOVE WORKPIECE B TO WORK YARD → WAIT FOR OPERATION |
| OPERATION OF OPERATOR | OPERATIONAL INPUT (OPERATION OF MASTER ARM) → NOTIFY GRIP COMPLETION OF WORKPIECE A | | OPERATIONAL INPUT (OPERATION OF MASTER ARM) → NOTIFY GRIP COMPLETION OF WORKPIECE B | |

FIG. 7

ROBOT SYSTEM

TECHNICAL FIELD

The present disclosure relates to a robot system utilizing a master-slave type robot.

BACKGROUND ART

Industrial robots have been developed in order to automate works, and contemplate labor saving, or an increase in work efficiency. The industrial robots are installed in a factory etc. as robots which carry out, for example, conveying, assembling, etc. of assembling components (workpiece). Here, when making the robot automatically assemble the assembling component, it is necessary to have a mechanism and control to measure a spatial relationship between the assembling component and an assembled component (product) by a sensor, and align the position and posture of the robot with sufficient accuracy. In particular, when the assembling component or the assembled component is a large-sized component and the robot automatically carries out the assembling work of the assembling component, a large number of sensors are needed in order to be able to correctly grasp a spatial relationship between the robot and the assembling component, or a spatial relationship between the assembling component and the assembled component. In addition, an advanced sensor recognition technology is also required for enabling highly-precise measurements in an extensive workspace. Thus, when the assembling component or the assembled component is a large-sized component and the robot automatically carries out the assembling work, cost increases, and errors or unintentional interferences occur in the assembling work if the work environment etc. changes even a bit, because the highly-precise measurements cannot be obtained.

Therefore, a remote operation control device which is capable of switching the operation to a manual operation in which a robot is operated based on an operating instruction from an operator is proposed, when a work environment etc. is changed while the robot automatically carries out a work (Patent Document 1). The remote operation control device according to Patent Document 1 is capable of detecting a deviation of an environmental model which is used as the base of an automatic operation of the robot when it is deviated from an actual work environment by more than a certain amount, and switching the operation from the automatic operation to the manual operation.

REFERENCE DOCUMENT OF CONVENTIONAL ART

Patent Document

[Patent Document 1] JP3924495B2

DESCRIPTION OF THE DISCLOSURE

Problems to be Solved by the Disclosure

One purpose of the present disclosure is to provide a robot system, which is capable of appropriately operating a slave arm in a process at which the slave arm is scheduled to operate in the automatic mode.

SUMMARY OF THE DISCLOSURE

According to one aspect of the present disclosure, a robot system is provided, which includes a master device configured to receive an operating instruction from an operator, a slave arm configured to perform, in a process containing a plurality of steps, processing of the step, a storage device configured to store operating sequence information that defines the processing carried out by the slave arm, and a control device configured to control operation of the slave arm. The control device includes a receiver configured to receive an input signal, a motion controller configured to determine whether an operating mode of the slave arm is to be an automatic mode in which the slave arm is operated based on the operating sequence information, or a manual mode in which the slave arm is operated based on the operating instruction inputted through the master device, or a correctable automatic mode in which the operation of the slave arm under operation in the automatic mode is corrected based on the operating instruction inputted through the master device, and control the operation of the slave arm in the determined operating mode, and a continuation determinator configured to determine whether a continuation of the automatic mode is permitted. In a process at which the slave arm is scheduled to operate in the automatic mode, after the motion controller suspends the operation of the slave arm in the automatic mode at a given step of the process, the continuation determinator determines whether the continuation of the automatic mode is permitted based on the input signal received by the receiver when the operation is suspended.

With the above configuration, since the master device and slave arm are provided, the operating instruction is transmitted from the operator, through the master arm, to the slave arm, so that a series of work is carried out.

Further, since the control device includes the motion controller, which operating mode the slave arm operates in among the automatic mode, the manual mode and the correctable automatic mode is determined so that the slave arm is controlled to operate in the appropriate operating mode.

Moreover, since the control device includes the continuation determinator, in the process at which the slave arm is scheduled to operate in the automatic mode, whether the continuation of the automatic mode is permitted is determined at the given step of the process. Therefore, for example, when all the steps included in the process cannot be completed by the time until which the automatic mode is scheduled to continue as it is, or a processing to be performed at or after the next step cannot be performed with sufficient accuracy in the automatic mode, it is possible to change the operating mode of the slave arm to other modes such as the manual or correctable automatic mode so as to continue the process. Further, when various kinds of products are assembled in a same production line, even if some kind of product is difficult to assemble in the automatic mode, it is possible to change the operating mode of the slave arm to other modes such as the manual or correctable automatic mode so as to continue the process.

On the contrary, if suitable processing is performed by the operation of the slave arm in the automatic mode, it is possible to continue the operation of the slave arm in the automatic mode without changing the mode.

Therefore, the robot system according to the present disclosure provides an effect that the slave arm is capable of being appropriately operated in the process at which the slave arm is scheduled to be operated in the automatic mode.

The robot system according to the aspect of the present disclosure described above may include an output device configured to output information to be notified to the operator. After the motion controller suspends the operation of the slave arm in the automatic mode at the given step, the output device may output an inquiry of whether the continuation of the automatic mode is permitted as the information to be notified to the operator. The continuation determinator may determine whether the continuation of the operation of the slave arm in the automatic mode is permitted based on the input signal received by the receiver according to the output of the inquiry by the output device.

With the above configuration, since the output device is provided, the inquiry of whether the continuation of the operation of the slave arm in the automatic mode is permitted can be outputted to the operator. Further, the continuation determinator is capable of determining whether the continuation of the automatic mode is permitted based on the input signal received by the receiver according to the inquiry.

Therefore, the robot system according to the aspect of the present disclosure, whether the continuation of the automatic mode is permitted can be determined by reflecting the operator's determination.

In the robot system according to the aspect of the present disclosure described above, the master device may include a master arm configured to input the operating instruction into the slave arm, and a switch or a mobile terminal configured to input the input signal.

Here, as the mobile terminal, a tablet computer is considered for example.

With the above configuration, since the input of the input signal is performed by the switch or the mobile terminal etc., the operator can easily perform the input operation of the input signal.

The robot system according to the aspect of the present disclosure described above may further include a status information acquiring part configured to acquire status information indicative of a status of the slave arm in a workspace. The receiver may receive the status information acquired by the status information acquiring part as the input signal. After the motion controller suspends the operation of the slave arm in the automatic mode at the given step, the continuation determinator may determine whether the continuation of the operation of the slave arm in the automatic mode is permitted based on the status information received by the receiver.

With the above configuration, since the status information acquiring part is provided, it is possible to grasp the status of the slave arm in the workspace where the slave arm works. Note that, the status of the slave arm includes, for example, a stopping position and a stopping posture of the slave arm at the time of completion of a given step, or a completion time of the give step.

Further, the continuation determinator is capable of determining whether the continuation of the operation of the slave arm in the automatic mode is permitted based on the status information received by the receiver from the status information acquiring part. Therefore, whether the continuation of the automatic mode is permitted can be determined according to the status of the slave arm at the time of completion of the given step. Moreover, since the continuation determinator determines whether the continuation of the automatic mode is permitted based on the status information, the process of inquiring the operator of whether the continuation of the automatic mode is permitted can be omitted.

Further, in the robot system according to the aspect of the present disclosure described above, when the continuation determinator determines that the continuation of the operation of the slave arm in the automatic mode is not permitted, the output device may output the inquiry of the operating mode of the slave arm as the information to be notified to the operator. The motion controller may determine the operating mode of the slave arm at and after a subsequent step of the given step based on the input signal received by the receiver according to the output of the inquiry of the operating mode by the output device.

With the above configuration, since the output device outputs the inquiry of the operating mode of the slave arm, new operating mode can be inquired to the operator. Further, the motion controller is capable of determining the operating mode based on the input signal received by the receiver according to the output of the inquiry. Therefore, the operating mode is changed to the mode on which the operator's instruction is reflected, and at a step after the given step, the slave arm is capable of being operated in the operating mode after the change.

Further, in the robot system according to the aspect of the present disclosure described above, the output device may output the inquiry of the operating mode of the slave arm by sound, light, or vibration.

Since the output mode from the output device can be sound, light, or vibration, the inquiry of the operating mode of the slave arm can be outputted to the operator in a suitable mode.

Effect of the Disclosure

The present disclosure is configured as described above, and it provides an effect that the slave arm is capable of being appropriately operated in the process at which the slave arm is scheduled to be operated in the automatic mode.

BRIEF DESCRIPTION OF DRAWINGS

FIG. 3 is a view illustrating one example of an operating sequence of the robot system according to Example 1 of the embodiment of the present disclosure.

FIG. 7 is a view illustrating one example of an operating sequence of the robot system according to Example 2 of the embodiment of the present disclosure.

Figure 1:
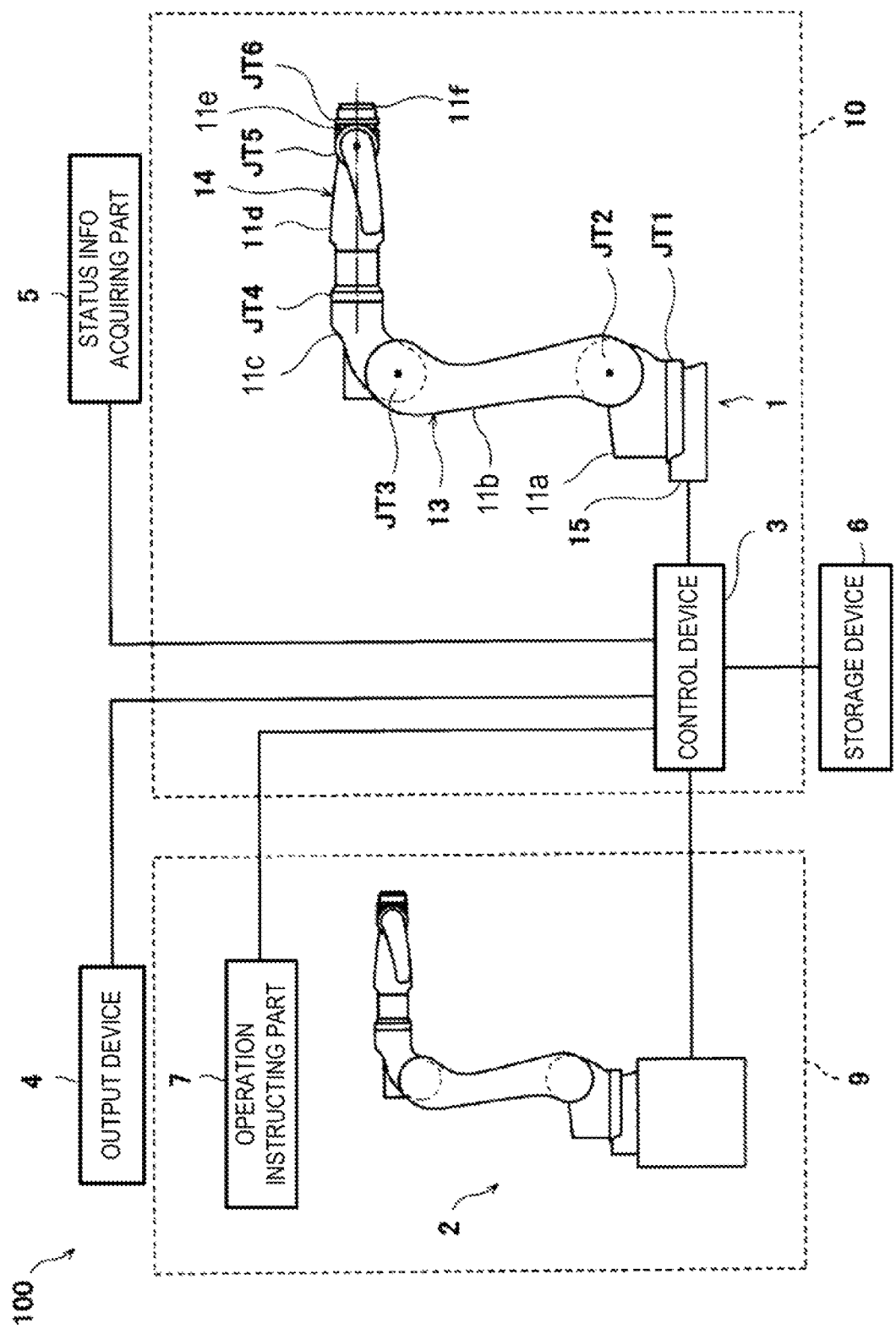
FIG. 1 is a schematic view illustrating one example of a configuration of a robot system according to one embodiment of the present disclosure.

MODES FOR CARRYING OUT THE DISCLOSURE (Outline of the Present Disclosure)

The present inventors have diligently studied a system which realizes a collaborated work of a human and a robot. Especially, they examined a system which realizes the collaborated work of a human and a robot utilizing a robot system using a master-slave type robot comprised of a master device and a slave robot having a slave arm.

First, a work comprised of a series of processings can be carried out by the robot system utilizing the master-slave type robot. Especially, during the work, the slave arm may be operated in a manual mode according to an operating instruction from an operator, which is inputted through the master device, at a process which requires the advanced sensor recognition technology etc. described above, and the slave arm may be operated in an automatic mode at other processing.

Meanwhile, they noticed that in a scene of operating the slave arm in the automatic mode comprised of a plurality of steps, there is a case of requiring a judgment of whether the automatic mode is to be continued as it is, or the operating mode needs to be changed, after the slave arm is operated in the automatic mode up to a given step.

Here, the conventional remote operation control device disclosed in Patent Document 1 has a configuration which is capable of, when there is an unexpected obstacle in the work environment, i.e., when an abnormality occurs in the work environment, detecting the abnormality and switching the operation of the robot from the automatic operation to the manual operation. However, they noticed that in the conventional remote operation control device, a configuration of determining whether the automatic mode is to be continued, after the slave arm is operated in the automatic mode up to a given step of a certain process, had not been taken into consideration. In addition, they also noticed that in the conventional remote operation control device, a configuration of determining whether the automatic mode is to be continued and inquiring the operator for a change from the automatic mode to another operating mode, had not been taken into consideration.

Thus, the present inventors acquired the following knowledge, as a result of repeated diligent examinations for those problems. That is, when the slave arm carries out a process comprised of a plurality of steps in the automatic mode, a control device which controls operation of the slave arm stops the operation of the slave arm in the automatic mode at a given step, and then waits for a signal input. In addition, the control device is configured to determine whether the automatic mode is to be continued based on the inputted signal. In addition, when determined that the automatic mode is not to be continued, the control device is configured to wait for a switching instruction of the operating mode from the operator.

Thus, during the operation of the slave arm in the automatic mode, it is determined whether the automatic mode is to be continued, and if determined that the automatic mode is not to be further continued, a suitable operating mode is inquirable to the operator.

Hereinafter, embodiments of the present disclosure will be described with reference to the drawings. Note that, below, the same reference characters are assigned to the same or corresponding components throughout the figures to omit redundant description.

Embodiment

First, a robot system 100 according to one embodiment of the present disclosure is described with reference to FIG. 1. FIG. 1 is a schematic view illustrating one example of a configuration of the robot system 100 according to the embodiment of the present disclosure.

The robot system 100 according to the embodiment of the present disclosure is a system utilizing a master-slave type robot. That is, in the robot system 100, the operator who is located at a position distant from a workspace (outside of workspace), for example, is able to move a master arm 2 provided to the master device 9 to make the slave arm 1 installed in the workspace perform an operation following the motion of the master arm 2 to perform a specific work. In addition, in the robot system 100, the slave arm 1 is also capable of automatically performing a given work without an intervention of the operation of the master arm 2 by the operator.

The operating mode in which the slave arm 1 is operated according to the operating instruction (instruction) inputted through the master arm 2 is herein referred to as "the manual mode." Note that "the manual mode" described above also includes a case where part of the operation of the slave arm 1 under operation is automatically corrected based on the operating instruction inputted by the operator operating the master arm 2. For example, the following operation may be included in such a case where the operation is corrected. That is, when the manual mode is set, the motion of the slave arm 1 may shake due to the shaking of the operator's hands etc. In such a case, the motion of the slave arm 1 may be automatically corrected so that the shaking is prevented.

Moreover, the operating mode in which the slave arm 1 is automatically operated according to preset task program(s) is herein referred to as "the automatic mode."

Further in the robot system 100 of this embodiment, it is configured so that, when the slave arm 1 operates in the automatic mode, the operation which is scheduled to be performed automatically is correctable by reflecting the operating instruction inputted through the master arm 2 on the operation of the slave arm 1. The operating mode in which the slave arm 1 is operated according to the preset task program while the operating instruction inputted through the master arm 2 is reflectable is herein referred to as "the correctable automatic mode." Note that "the automatic mode" described above is distinguished from "the correctable automatic mode" in that the operation of the master arm 2 is not reflected on the operation of the slave arm 1 when the operating mode in which the slave arm 1 is operated is the automatic mode.

[Configuration of Robot System According to the Embodiment]

As illustrated in FIG. 1, the robot system 100 has a configuration provided with a slave robot 10, a master device 9, an output device 4, a status information acquiring part 5, and a storage device 6. Note that, although not illustrated in particular in FIG. 1, the robot system 100 is further provided with a monitoring display device for the operator to check a work status by the slave arm 1, and a monitoring camera which images the work status of the slave arm 1. Note that the monitoring display device is installed in a space where the master device 9 is provided, the monitoring camera is installed in a space where the slave arm 1 is provided, and both the display device and the camera are connected wiredly or wirelessly.

(Configuration of Slave Robot)

The slave robot 10 includes the slave arm 1, an end effector (not illustrated) attached to a tip end of the slave arm 1, and the control device 3 which governs the operations of the slave arm 1 and the end effector.

(Slave Arm)

The slave arm 1 performs processing of steps among the plurality of steps. That is, a certain work is comprised of a plurality of processes for which the operating mode of the slave arm 1 is set, respectively, and each process includes a plurality of steps. The slave arm 1 carries out the processing of the step in the operating mode set to the step.

The slave arm 1 includes a pedestal 15, an arm part 13 supported by the pedestal 15, and a hand part 14 which is supported by the tip end of the arm part 11 and to which the end effector is attached. The slave arm 1 is an articulated robot arm having three or more joints JT1-JT6 as illustrated in FIG. 1, and is constructed by sequentially coupling a plurality of links 11a-11f. In more detail, at the first joint JT1, the pedestal 15 and a base-end part of the first link 11a are rotatably coupled about an axis extending in the vertical directions. At the second joint JT2, a tip-end part of the first link 11a and a base-end part of the second link 11b are rotatably coupled about an axis extending in horizontal directions. At the third joint JT3, a tip-end part of the second link 11b and a base-end part of the third link 11c are rotatably coupled about an axis extending in horizontal directions. At the fourth joint JT4, a tip-end part of the third link 11c and a base-end part of the fourth link 11d are rotatably coupled about an axis extending in longitudinal directions of the fourth link 11d. At the fifth joint JT5, a tip-end part of the fourth link 11d and a base-end part of the fifth link 11e are rotatably coupled about an axis perpendicular to the longitudinal directions of the link 11d. At the sixth joint JT6, a tip-end part of the fifth link 11e and a base-end part of the sixth link 11f are rotatably coupled in a twisting manner. A mechanical interface is provided to a tip-end part of the sixth link 11f. An end effector corresponding to the work type is mounted attachably and detachably to the mechanical interface.

The arm part 11 of the slave arm 1 is formed by a coupled body of the links and joints, which is comprised of the first joint JT1, the first link 11a, the second joint JT2, the second link 11b, the third joint JT3, and the third link 11c. Moreover, the hand part 14 of the slave arm 1 is formed by a coupled body of the links and joints, which is comprised of the fourth joint JT4, the fourth link 11d, the fifth joint JT5, the fifth link 11e, the sixth joint JT6, and the sixth link 11f.

Drive motors M1-M6 are provided to the joints JT1-JT6, respectively, as one example of an actuator which relatively rotates two members connected by each joint. The drive motors M1-M6 are, for example, servo motors which are servo-controlled by the control device 3. Moreover, the joints JT1-JT6 are provided with rotary sensors E1-E6 for detecting rotational positions of the drive motors M1-M6, and current sensors C1-C6 for detecting current which controls the rotation of the drive motors M1-M6. The rotary sensors E1-E6 are, for example, encoders. Note that, the drive motors M1-M6, the rotary sensors E1-E6, and the current sensors C1-C6 are described by alphabets with suffixes 1-6 corresponding to the respective joints JT1-JT6. Below, when an arbitrary joint among the joints JT1-JT6 is illustrated, the suffix is excluded and it is referred to as "JT," and the same is applied to the drive motor M, the rotary sensor E, and the current sensors C1-C6.

Note that the above configuration of the slave arm 1 is one example, the configuration of the slave arm 1 is not limited to the above configuration, and the configuration may suitably be changed according to the type, the workspace, etc. of the work which are carried out by using the slave arm 1.

(Control Device)

Figure 2:
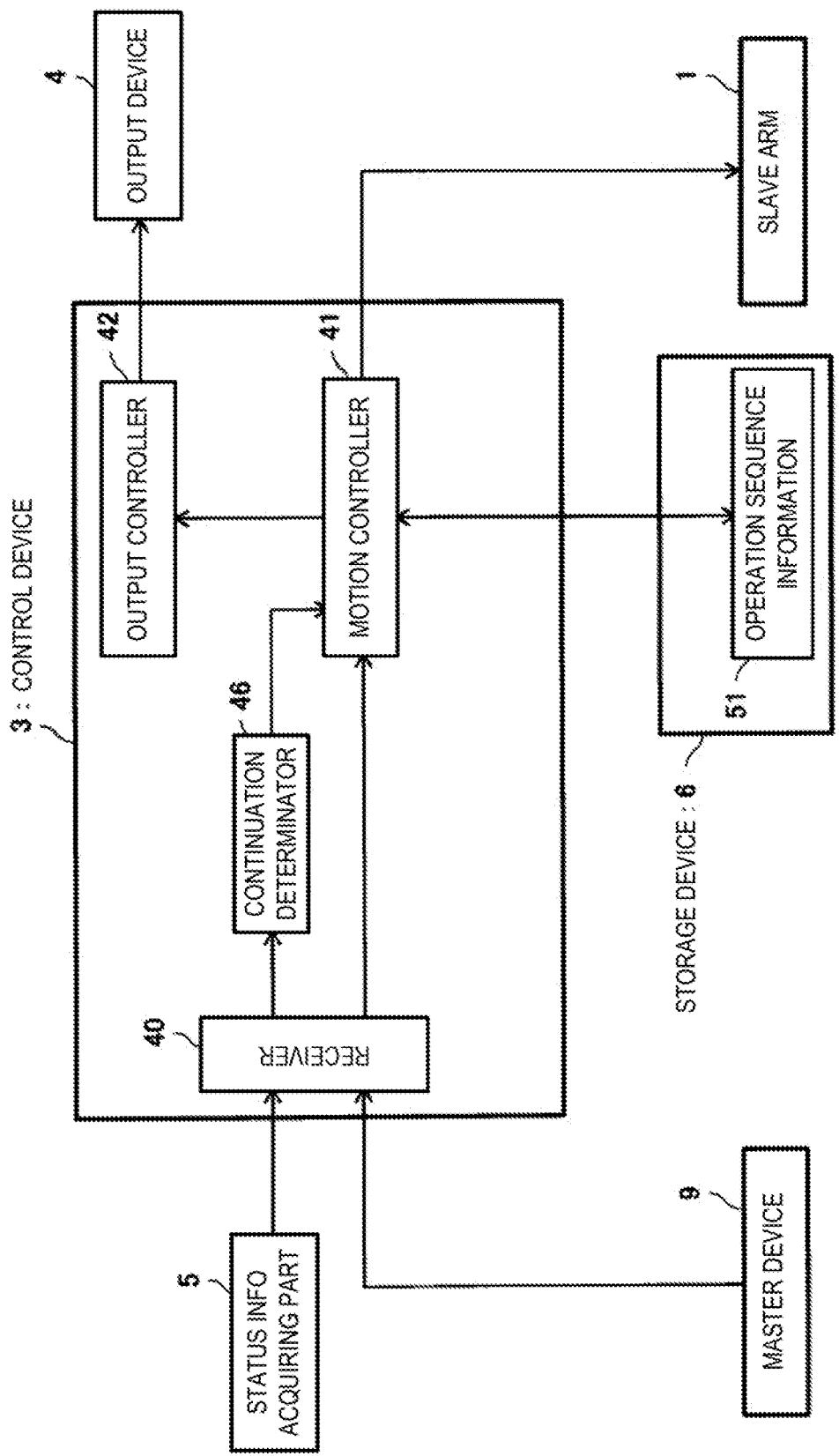
FIG. 2 is a block diagram illustrating one example of a functional structure according to a control device provided to the robot system illustrated in FIG. 1.

Next, the control device 3 which controls the operation of the slave arm 1 having the configuration described above is described with reference to FIG. 2. FIG. 2 is a block diagram illustrating one example of a functional structure according to the control device 3 provided to the robot system 100 illustrated in FIG. 1.

The control device 3 is to control the operation of the slave arm 1, and as illustrated in FIG. 2, it includes a receiver 40, a motion controller 41, an output controller 42, and a continuation determinator 46, as its functional blocks. The control device 3 may be comprised of, for example, an arithmetic operator (not illustrated) comprised of a micro controller, a MPU, a PLC (Programmable Logic Controller), a logic circuit, etc., and a memory (not illustrated) comprised of a ROM, a RAM, etc. Alternatively, each functional block provided to the control device 3 may be implemented by the arithmetic operator of the control device 3 reading and executing control program(s) stored in the memory.

The receiver 40 is to receive an input signal transmitted from the outside of the control device 3. The input signal received by the receiver 40 includes, for example, a signal transmitted from the master device 9 (operational input signal) or a signal transmitted from the status information acquiring part 5.

The motion controller 41 determines whether the operating mode of the slave arm 1 is to be the automatic mode in which the slave arm 1 is operated based on operating sequence information 51, or whether it is to be the manual mode in which the slave arm 1 is operated based on the operating instruction inputted through the master arm 2 of the master device 9, or whether it is to be the correctable automatic mode in which the operation of the slave arm under operation in the automatic mode is corrected based on the operating instruction inputted through the master arm 2 of the master device 9. The motion controller 41 then controls the operation of the slave arm 1 according to the determined operating mode.

For example, when the receiver 40 receives from the master device 9 the operational input signal indicative of the operating instruction for the subsequent process as the input signal, the motion controller 41 may determine the operating mode of the subsequent process which is carried out by the slave arm 1 by using this operational input signal as a trigger. Alternatively, when an automatic switching of the operating mode is set, the motion controller 41 may determine the operating mode of the subsequent process of the slave arm 1 by referring to the operating sequence information 51 stored in the storage device 6.

The motion controller 41 controls the slave arm 1 to be operated in the determined operating mode when the operating mode is determined. When the motion controller 41 determines that the slave arm 1 is to be operated in the automatic mode, it reads out the operating sequence information 51, and controls the slave arm 1 to carry out the operation defined by the operating sequence information 51. On the other hand, when the motion controller 41 determines that the slave arm 1 is to be operated in the manual mode, it controls the slave arm 1 to be operated based on the operating instruction which the receiver 40 received from the master arm 2. Moreover, when the motion controller 41 determines that the slave arm 1 is to carry out the correctable automatic operation, it controls the slave arm 1 so that the operation in the automatic mode of the slave arm 1 becomes a corrected operation based on the operating instruction inputted through the master arm 2.

Note that, if the slave arm 1 is operated in the automatic mode, the motion controller 41 may be configured to transmit information indicative of the termination of the automatic mode to the output controller 42 when the operation in the automatic mode is terminated.

The output controller 42 controls the output device 4 to output information to be notified to the operator etc. For example, when the output controller 42 receives the information indicative of the termination of the automatic mode from the motion controller 41, it controls the output device 4 to output this information. The output device 4 may be configured, according to a control instruction from the output controller 42, to display the notice of the termination of the automatic mode of the slave arm 1, or output the same by sound or light. If configured in this way, the operator can grasp the termination of the operation in the automatic mode of the slave arm 1.

Further, the output controller 42 may be configured, when the status information is received from the status information acquiring part 5, to control the output device 4 to output this status information. When it is configured in this way and the output device 4 is the display device, the operating status etc. of the slave arm 1 can be displayed on the output device 4. Thus, the operator can monitor the operating status etc. of the slave arm 1.

(Status Information Acquiring Part)

The status information acquiring part 5 acquires the status information indicative of the status in the workspace of the slave arm 1. The status information includes information utilized in order to recognize the position, posture, or the like of the slave arm 1 in the workspace, or the status around the slave arm 1. More specifically, the status information includes information required in order to enable recognition of the status of the slave arm 1 in the workspace and the status around the slave arm 1, for example, the position or posture of the slave arm 1 in the workspace, the spatial relationship between the slave arm 1 and the workpiece, or the spatial relationship between the slave arm 1 and the assembled component to which the workpiece is attached. The status information acquiring part 5 may be implemented by, for example, a sensor, an imaging device, a communication apparatus, an encoder, etc. The sensor includes, for example, a laser sensor, a radar sensor, or the like for measuring the distance or the position to the workpiece (the assembling component) or the assembled component. Further, it also includes a stereoscopic camera which is a sensor for measuring the distance from the slave arm 1 to an object therearound by using image data obtained from a plurality of imaging devices. The communication apparatus includes, for example, a communication apparatus which acquires information from the workpiece (the assembling component) or the assembled component, or a sensor and the imaging device installed at a given position in the workspace. The encoder includes, for example, an encoder which can detect an amount of movement or the position of the slave arm.

Moreover, the status information acquired by the status information acquiring part 5 is not limited to the information utilized in order to recognize the position and/or posture of the slave arm 1 in the workspace, or the status around the slave arm 1, which are described above.

For example, the status information acquired by the status information acquiring part 5 may be, for example, information indicative of a lapsed time of the work currently carried out by the slave arm 1. When the status information is information indicative of the lapsed time of the work currently carried out by the slave arm 1, the status information acquiring part 5 may be a measuring device for measuring a period of time for which the slave arm 1 takes to process a given step.

The status information acquiring part 5 sequentially acquires the status information, and the acquired status information is inputted into the control device 3, and the control device 3 utilizes it for the motion control of the slave arm 1. Further, the control device 3 may also be configured to control the output device 4 to output the status information. The status information acquiring part 5 may be attached to the slave arm 1 itself, or may be installed at a suitable position in the workspace. Moreover, the number of status information acquiring parts 5 installed may be one, or may be more. The installed position and number are arbitrary, as long as a suitable number of status information acquiring parts 5 are installed at positions where they are able to acquire the status information appropriately.

(Output Device)

The output device 4 outputs the information transmitted from the control device 3, and may be implemented by a display device, a speaker, a light source, a printer, an oscillation generating device, etc. For example, when the output device 4 is the display device, the output device 4 displays the information transmitted from the control device 3. For example, when the output device 4 is the speaker, the output device 4 outputs the information transmitted from the control device 3 as sound. When the output device 4 is the light source, the output device 4 outputs the information transmitted from the control device 3 as light. When the output device 4 is the printer, the output device 4 prints out the information transmitted from the control device 3. When the output device 4 is the oscillation generating device, the output device 4 outputs the information transmitted from the control device 3 as vibration. The output device 4 is provided at a suitable position where the operator of the master device 9 is detectable of the outputted information.

(Storage Device)

The storage device 6 is a readable and writable recording medium, and stores the operating sequence information 51 on the robot system 100. The operating sequence information 51 is the task program which defines the operation of the slave arm 1, and includes information related to the operating sequence which defines the processing of each step carried out by the slave arm 1 in the workspace. Specifically, in the robot system 100 according to this embodiment, it is information that the operation order, the operating mode of the slave arm 1, and an operation flow of each process are associated with each other, as illustrated in FIG. 3. FIG. 3 is a view illustrating one example of the operating sequence of the robot system 100 according to Example 1 of the embodiment of the present disclosure.

Moreover, the storage device 6 may store a scheduled route information (not illustrated) indicative of a scheduled route range of the slave arm 1. Note that the scheduled route information may include, for example, time-series information, such as the position, the posture, etc. of the slave arm 1 which is scheduled for carrying out each process of a series of work. Thus, when it is configured so that the scheduled route information is stored in the storage device 6, the information can be utilized in order to detect whether the slave arm 1 is deviated from the scheduled route range.

Note that, in the robot system 100 according to the embodiment, although the storage device 6 is provided separately from the control device 3 but it may be provided integrally with the control device 3.

(Master Device)

The master device 9 is installed outside the workspace, and is an input device which receives the operating instruction from the operator and is provided with the master arm 2 and an operation instructing part 7.

In the robot system 100, when the operator moves the master arm 2, the slave arm 1 moves so as to follow the motion of the master arm 2. Since the master arm 2 has the similar structure to the slave arm 1, the configuration of the master arm 2 is omitted. Note that the master arm 2 may be, for example, an input device (a joy stick) in which a directional input is possible by a lever, which has a non-similar structure to the slave arm 1.

The manual operation information is generated by the operator moving the master arm 2, and the information is sent to the control device 3. In the robot system 100 according to this embodiment, when the operating mode in which the slave arm 1 is operated is the manual mode, the operational input signal is sent to the control device 3 as the input signal inputted through the master arm 2, and the slave arm 1 moves so as to follow the motion of the master arm 2 by the control instruction from the control device 3 based on the operational input signal. Moreover, for example, when the operating mode in which the slave arm 1 is operated is the correctable automatic mode, the operational input signal is sent from the master arm 2 to the control device 3, and the operation of the slave arm 1 under automatic operation by the control instruction from the control device 3 is corrected by the operational input signal.

The operation instructing part 7 is an input device which is installed outside the workspace similar to the master arm 2, receives the operating instruction from the operator, and transmits the received operating instruction to the control device 3 of the slave arm 1 as the operational input signal. The operation instructing part 7 may include an input switch for receiving an operator's operating instruction, or a mobile terminal, such as a tablet computer.

Note that the operational input signal transmitted from the master device 9 to the control device 3 of the slave arm 1 may include, in addition to the signal inputted by the operator through the master arm 2, a signal inputted by the operator through the operation instructing part 7.

(Operating Sequence of Robot System)

Next, the operating sequence of the work comprised of the series of processings which can be carried out by the robot system 100 having the configuration described above is described using the following Examples 1 and 2.

EXAMPLE 1

Figure 4:
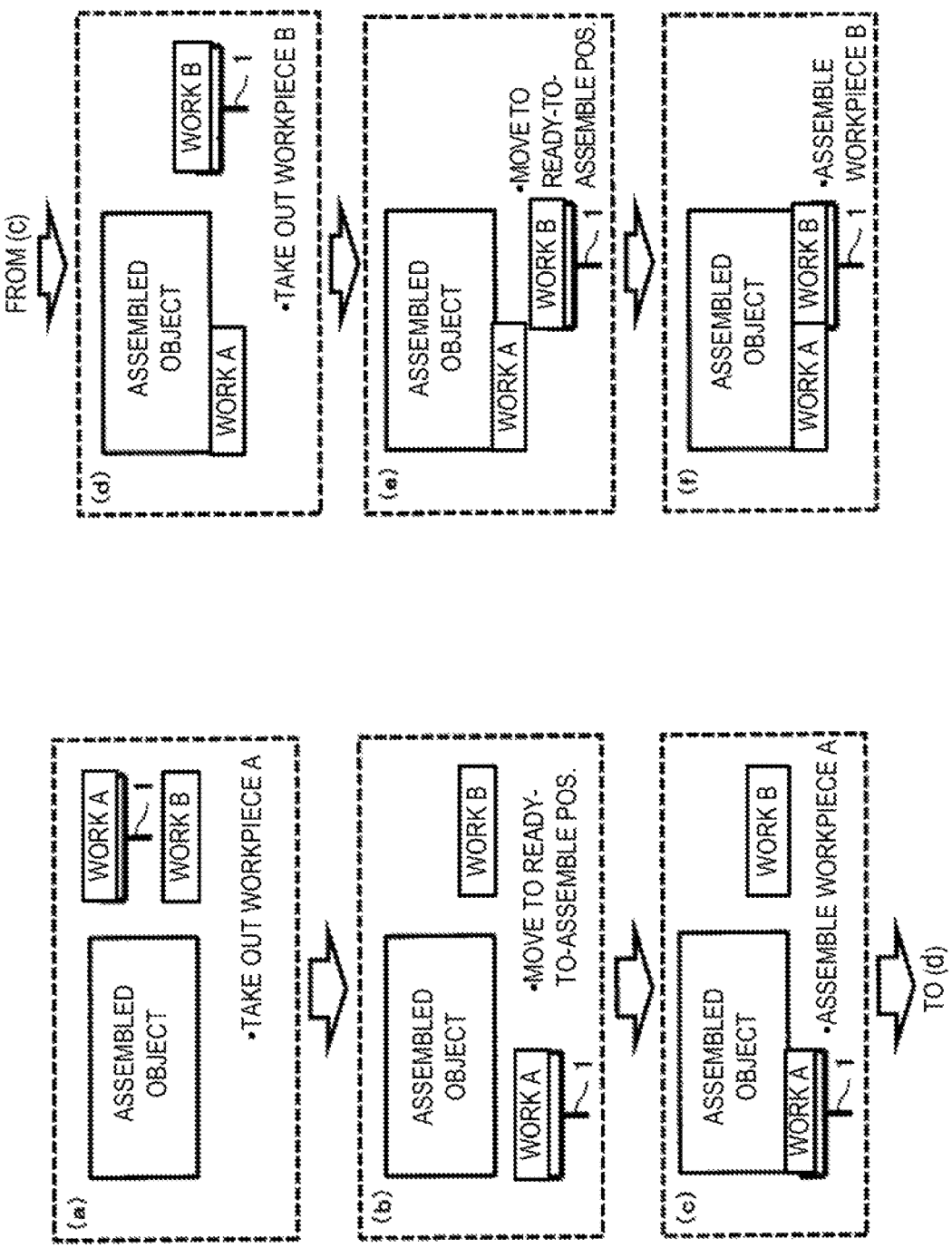
FIG. 4 is a view schematically illustrating one example of a slave arm which carries out a work following the operating sequence illustrated in FIG. 3.
Figure 5:
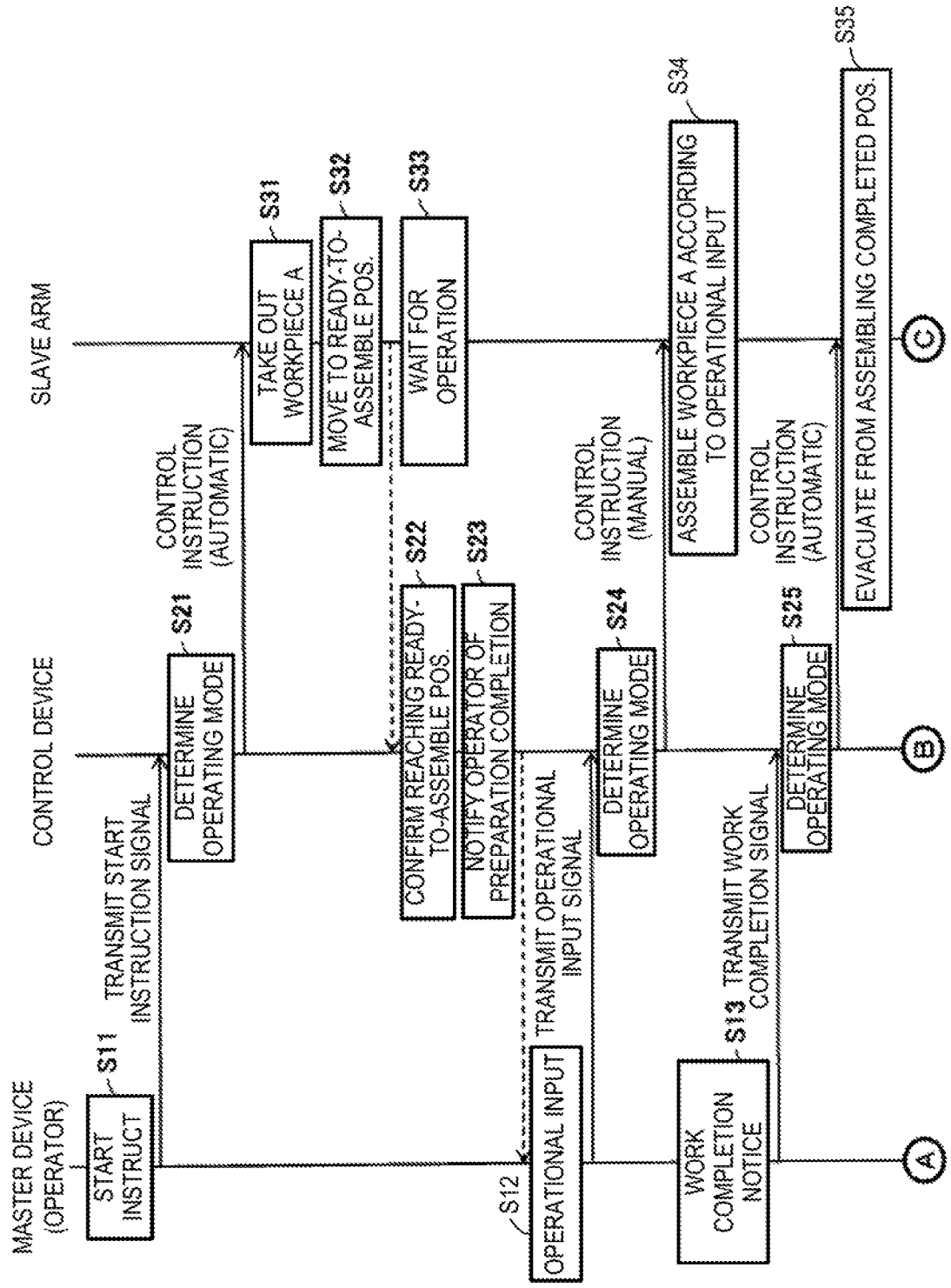
FIG. 5 is a flowchart illustrating one example of operation processing in a master device, the control device, and the slave arm, which carry out the operating sequence illustrated in FIG. 3, respectively.
Figure 6:
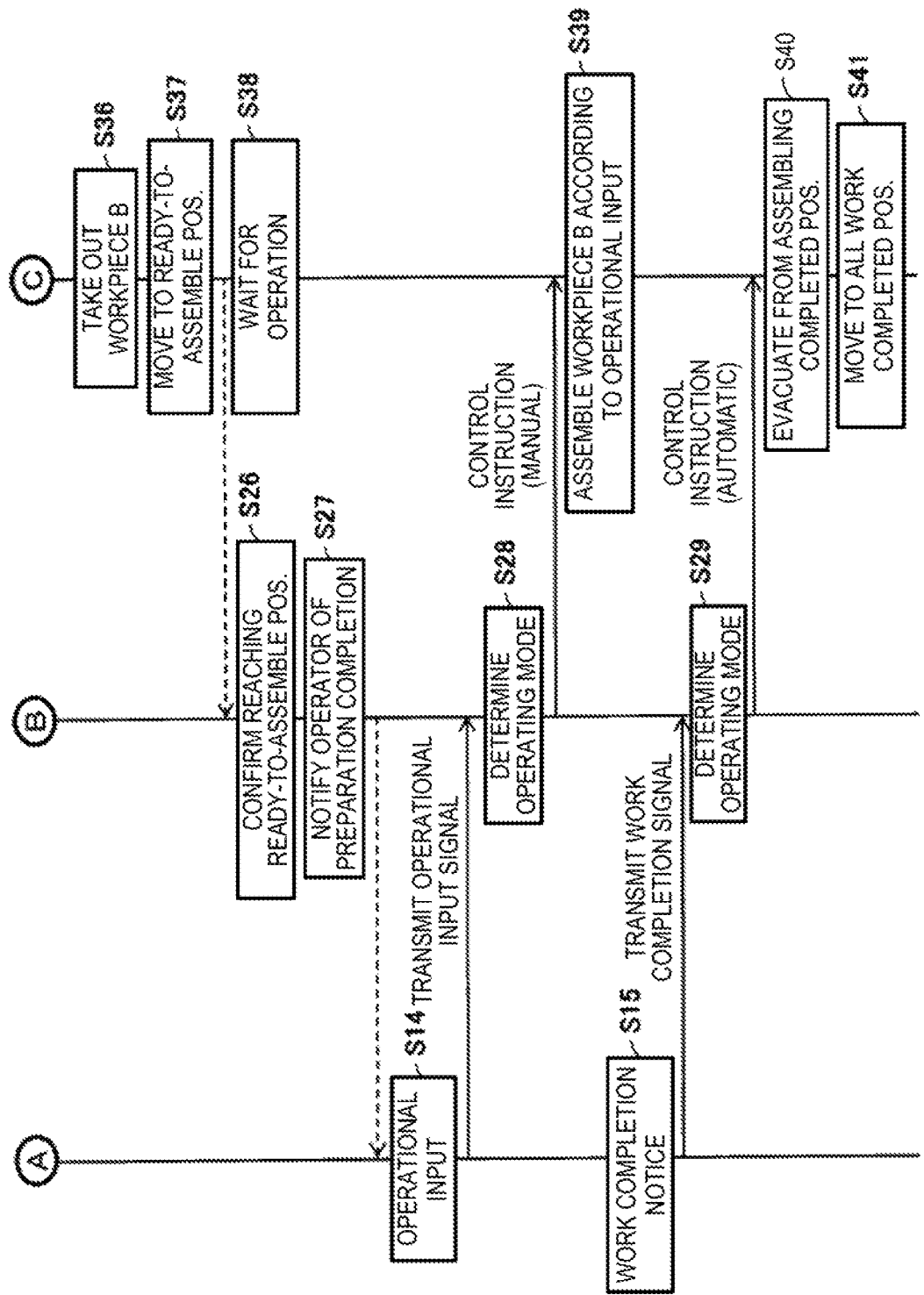
FIG. 6 is a flowchart illustrating one example of the operation processing in the master device, the control device, and the slave arm, which carry out the operating sequence illustrated in FIG. 3, respectively.

Referring to FIGS. 4 to 6 in addition to FIG. 3, the operating sequence of the robot system 100 according to Example 1 of the embodiment of the present disclosure is described. FIG. 4 is a view schematically illustrating one example of the slave arm 1 which carries out a work following the operating sequence illustrated in FIG. 3. FIGS. 5 and 6 illustrate a flowchart of one example of operation processings in each of the master device 9, the control device 3, and the slave arm 1, which carry out the operating sequence illustrated in FIG. 3.

In Example 1, the operating sequence of the robot system 100 is described using an assembling work of a workpiece to an assembled object as one example. Herein, the entire operating sequence illustrated in FIG. 3 is referred to as a work, and each processing illustrated by <1> to <5> in FIG. 3 is referred to as a process. Moreover, processing carried out at each process is referred to as a step. In FIG. 3, <1> to <5> indicate a performing order of the processes in the work.

Note that the robot system 100 is configured so that the slave arm 1 operates following the operating sequence described above by executing the operating sequence information 51 as the task program. In the operating sequence related to the work of Example 1, the slave arm 1 carries out a movement from a position where the workpiece is stored to a position near an assembling position of the workpiece (ready-to-assemble position) in the automatic mode. It is designed so that, when the slave arm 1 brings the workpiece to the ready-to-assemble position, since the positioning at the assembling position and the assembling work are complicated for the assembling of the workpiece to the assembled object, the slave arm 1 carries out the assembling in the manual mode according to the operating instruction from the operator.

This operating sequence related to the work of Example 1 is applicable to a rigging process of an automobile where the assembled object is a vehicle body, a workpiece A is a front seat, and a workpiece B is a rear seat. Moreover, it is also applicable to an assembling process of a robot where the assembled object is an arm, the workpiece A is a transmission, and the workpiece B is a motor.

Note that, for convenience of explanation, although Example 1 to Example 4 are described below, using the assembling work of the workpiece to the assembled object is described as one example, but the work which is carried out by using the robot system 100 is not limited to the assembling work. For example, it may be a painting work to a workpiece. The painting work includes, for example, a painting work in which the slave arm 1 paints the workpiece conveyed into a paint area (not illustrated) by a conveyor device (not illustrated). Alternatively, it may also include a painting work in which the slave arm 1 paints while moving in order to paint a main body of a large-sized apparatus, such as a passenger aircraft.

First, as illustrated in FIG. 5, the operator operates the operation instructing part 7 of the master device 9 to input a start instruction (Step S11). That is, a start instruction signal which instructs a start of the operating sequence is transmitted from the master device 9 to the control device 3 as the operational input signal. In the control device 3, the receiver 40 waits for the operational input signal (start instruction signal), and when the receiver 40 receives the start instruction signal, the motion controller 41 determines the operating mode of the slave arm 1 (Step S21). The motion controller 41 may be configured to perform the determination of the operating mode of the slave arm 1 by referring to the operating sequence information 51 stored in the storage device 6. Alternatively, it may be configured so that information related to the operating mode of the slave arm 1 for the subsequent step is included in the start instruction signal transmitted from the master device 9, and the motion controller 41 performs the determination based on the information.

When determining the operating mode based on the operating sequence information 51 illustrated in FIG. 3, the motion controller 41 determines the operating mode as follows. That is, in the operating sequence information 51, the operating mode of the slave arm 1 is set to the automatic mode at the first operation order <1>. Then, the motion controller 41 determines that the operating mode of the slave arm 1 is the automatic mode, and controls the slave arm 1 to be operated in the automatic mode. That is, the motion controller 41 refers to the operating sequence information 51 and transmits the control instruction to the slave arm 1 so that the slave arm 1 carries out each step of the operation order <1>.

Specifically, according to the control instruction from the motion controller 41 (automatic mode), the slave arm 1 moves to an extraction position of the workpiece A, and extracts or takes out the workpiece A (Step S31). Here, a spatial relationship of the workpiece A, the assembled object, and the slave arm 1 is in a state illustrating in (a) of FIG. 4. When the workpiece A is taken out, the slave arm 1 moves to the ready-to-assemble position while holding the workpiece A, as illustrated in (b) of FIG. 4 (Step S32). When the slave arm 1 moves to the ready-to-assemble position, it waits for the operating instruction signal (an operation waiting state) (Step S33). Here, the operating instruction signal is an operational input signal transmitted to the slave arm 1 through the master device 9 (the master arm 2) when the slave arm 1 is operated by the operator in the manual mode.

Note that the motion controller 41 is capable of determining whether the slave arm 1 reaches the ready-to-assemble position based on the status information acquired from the status information acquiring part 5. In FIG. 5, a dashed-line arrow extending toward the upstream of Step S22 of the control device 3 from the downstream of Step S32 of the slave arm 1 represents an acquisition of the status information by the control device 3.

Then, when the motion controller 41 confirms that the slave arm 1 reaches the ready-to-assemble position (Step S22), it instructs the output controller 42 to report a completion of preparation for the assembling work to the operator. The output controller 42 controls the output device 4 to output information indicative of the completion of preparation for the assembling work according to the instruction from the motion controller 41 (Step S23). Here, the receiver 40 waits for the operational input signal transmitted from the master device 9 as the input signal. Note that, in FIG. 5, a dashed-line arrow extending toward the upstream of Step S12 of the master device 9 from the downstream of Step S23 of the control device 3 represents the detection of the notice of completion of preparation by the operator.

When the completion of preparation is notified by the output device 4, the operator inputs a switching instruction of the operating mode from the operation instructing part 7 of the master device 9, and then performs the operational input by using the master arm 2 of the master device 9 (Step S12). An operating mode switching signal from the operation instructing part 7 and the operational input signal from the master arm 2 are transmitted to the control device 3 as a result of these inputs. In the control device 3, when the receiver 40 receives the mode switching signal, the motion controller 41 determines the operating mode of the slave arm 1 (Step S24). Since the operating mode is the manual mode at the operation order <2> of the subsequent process, the motion controller 41 transmits to the slave arm 1 the control instruction based on the operational input signal inputted through the master arm 2. Thus, the slave arm 1 moves following the motion of the master arm 2. Specifically, the slave arm 1 carries out the assembling of the workpiece A to the assembled object, as illustrated in (c) of FIG. 4, according to the operational input signal inputted through the master arm 2 (Step S34). When the assembling of the workpiece A to the assembled object is completed, the operator operates the operation instructing part 7 of the master device 9 to input a notice of work completion (Step S13). A work completion signal is transmitted from the master device 9 to the control device 3 by the input of the notice of work completion.

When the receiver 40 receives the work completion signal, in the control device 3, the motion controller 41 determines the operating mode of the slave arm 1 for the subsequent process (Step S25). The motion controller 41 may be configured to perform the determination of the operating mode of the slave arm 1 by referring to the operating sequence information 51 stored in the storage device 6. Alternatively, it may be configured so that information related to the operating mode of the slave arm 1 for the subsequent step is included in the start instruction signal transmitted from the master device 9, and the motion controller 41 performs the determination based on the information.

In the example of the operating sequence information 51 illustrated in FIG. 3, the operating mode is set to the automatic mode in the operation order <3> for the subsequent process. Then, the motion controller 41 determines that the operating mode is the automatic mode, and refers to the operating sequence information 51 to transmit the control instruction to the slave arm 1 so that the slave arm 1 carries out each step of the operation order <3>.

Specifically, the slave arm 1 is evacuated from an assembling completed position of the workpiece A according to the control instruction from the motion controller 41 (Step S35). Then, the slave arm 1 takes out the workpiece B, as illustrated in (d) of FIG. 4 (Step S36). When the workpiece B is taken out, the slave arm 1 moves to the ready-to-assemble position while holding the workpiece B, as illustrated in (e) of FIG. 4 (Step S37). When the slave arm 1 moves to the ready-to-assemble position, it waits for the operating instruction signal (Step S38).

Note that the motion controller 41 may be configured to determine whether the slave arm 1 reaches the ready-to-assemble position based on the status information acquired from the status information acquiring part 5, similar to Step S32. In FIG. 6, a dashed-line arrow extending toward the upstream of Step S26 of the control device 3 from the downstream of Step S37 of the slave arm 1 represents the acquisition of the status information by the control device 3.

Then, when the motion controller 41 confirms that the slave arm 1 reaches the ready-to-assemble position (Step S26), it instructs the output controller 42 to notify the operator of the preparation for the assembling work having been completed. The output controller 42 controls the output device 4 to output information indicative of the completion of preparation for the assembling work (Step S27). Then, the receiver 40 waits for the operational input signal transmitted from the master device 9. Note that, in FIG. 6, a dashed-line arrow extending toward the upstream of Step S14 of the master device 9 from the downstream of Step S27 of the control device 3 represents that the operator detects the notice of completion of preparation outputted from the output device 4.

When the completion of assembling work preparation of the workpiece B is notified by the output device 4, the operator performs the operational input as well as the switching instruction of the operating mode, by using the master arm 2 and the operation instructing part 7 of the master device 9 (Step S14). The switching instruction of the operating mode and the operational input inputted through the master device 9 are transmitted to the control device 3 as the operating mode switching signal and the operational input signal. In the control device 3, when the receiver 40 receives the operating mode switching signal and the operational input signal, the motion controller 41 determines the operating mode of the slave arm 1 for the subsequent process (Step S28). In the example of the operating sequence information 51 illustrated in FIG. 3, the operating mode is set to the manual mode for the subsequent operation order <4>. Then, the motion controller 41 determines that the operating mode is the manual mode, and transmits to the slave arm 1 the control instruction (manual mode) based on the operational input signal received from the master arm 2. Thus, the slave arm 1 operates following the operation of the master arm 2. Specifically, the slave arm 1 carries out the assembling of the workpiece B to the assembled object, as illustrated in (f) of FIG. 4, according to the operational input from the master arm 2 (Step S39). When the assembling of the workpiece B to the assembled object is completed, the operator operates the operation instructing part 7 of the master device 9 to input the notice of work completion (Step S15). Then, the notice of work completion inputted by the operation instructing part 7 is transmitted to the control device 3.

When the receiver 40 of the control device 3 receives the work completion signal, the motion controller 41 determines the operating mode of the slave arm 1 for the subsequent process (Step S29). In the example of the operating sequence information 51 illustrated in FIG. 3, the operating mode is set to the automatic mode in the operation order <5>. Then, the motion controller 41 determines that the operating mode is the automatic mode, and it controls so that the slave arm 1 automatically carries out each step of the operation order <5> which is the subsequent process.

Specifically, the slave arm 1 is evacuated from the assembling completed position of the workpiece A according to the control instruction (automatic mode) from the motion controller 41 (Step S40). Then, the slave arm 1 moves to an all work completed position (Step S41).

As described above, the robot system 100 according to Example 1 of the embodiment of the present disclosure carries out the operating sequence related to the work comprised of the series of processings. Thus, in the work comprised of the series of processings, for example, the slave arm 1 is capable of carrying out a coarse operation in the automatic mode, and the slave arm 1 is capable of carrying out a fine operation in the manual mode in which the slave arm 1 operates according to the operational input from the operator.

As described above, the determination of the operating mode by the motion controller 41 may be made by referring to the operating sequence information 51, using the receiver 40 receiving the start instruction signal, the operational input signal, or the work completion signal transmitted from the master device 9, as a trigger. Alternatively, information indicative of the operating mode to be carried out at the subsequent process may be included in the start instruction signal, the operational input signal, or the work completion signal, and the motion controller 41 may be configured to determine the operating mode based on the information indicative of the operating mode included in these signals transmitted from the master device 9. When the motion controller 41 is configured to determine the operating mode based on the signal transmitted from the master device 9, it is not necessary to include the information related to the operating mode in the operating sequence information 51 stored in the storage device 6.

Note that, in the operating sequence described above, the example in which the slave arm 1 operates automatically from the first process (the operation order <1>) is described. That is, the operating sequence described above is a sequence example in which it is assumed that the control device 3 has performed an external-world recognition of the environment which surrounds the slave arm 1 at the work start timing of the slave arm 1. However, at the work start timing of the slave arm 1, the control device 3 may have not performed the external-world recognition of the environment which surrounds the slave arm 1. In such a case, it may be an operating sequence in which the slave arm 1 is first moved in the manual mode to a position where the control device 3 is able to carry out the external-world recognition, and the mode is then switched from the manual mode to the automatic mode. Below, an operating sequence in which the control device 3 has not been able to carry out the external-world recognition of the environment which surrounds the slave arm 1 at the work start timing of the slave arm 1, is described as Example 2.

EXAMPLE 2

Figure 8:
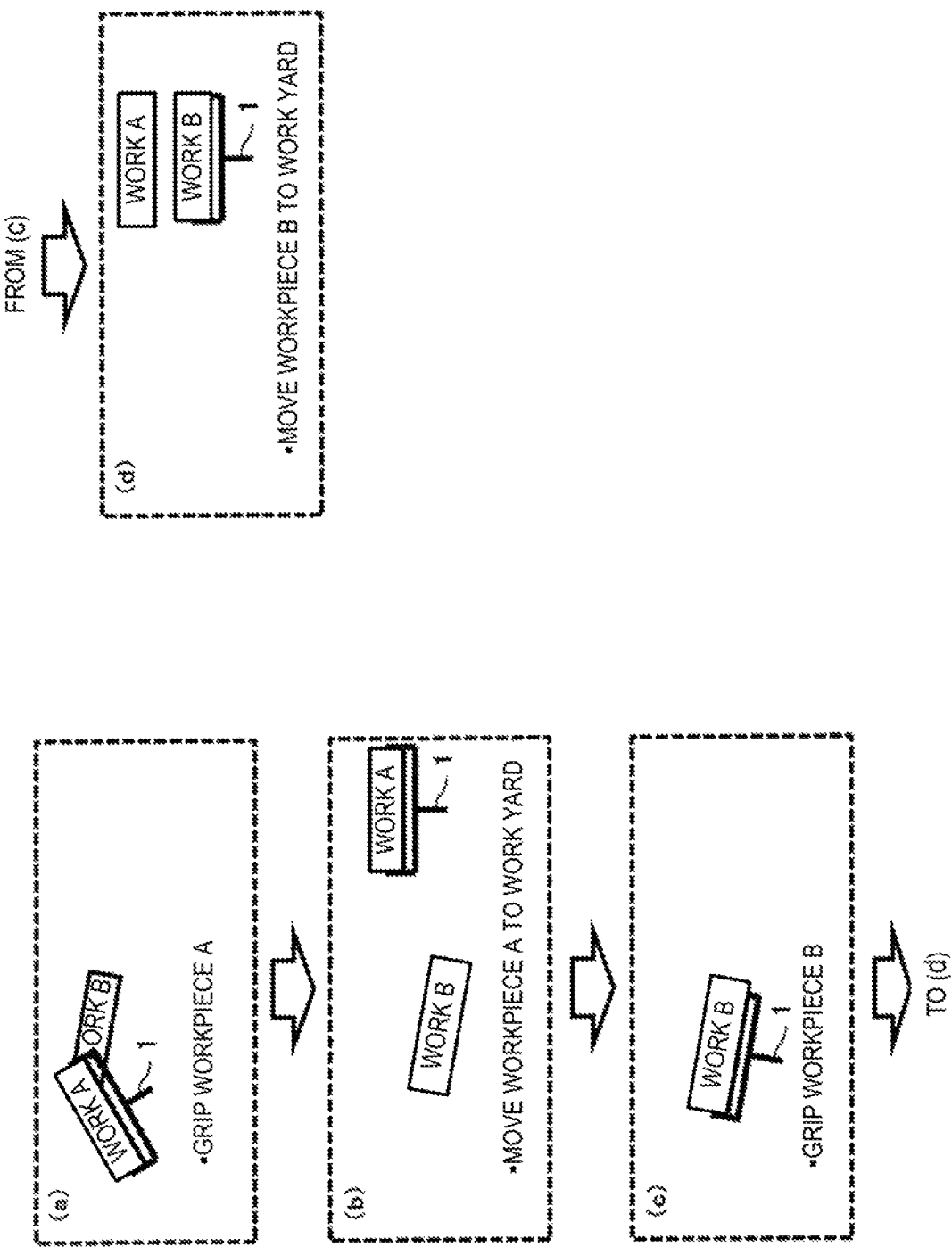
FIG. 8 is a view schematically illustrating one example of the slave arm which carries out a work following the operating sequence illustrated in FIG. 7.
Figure 9:
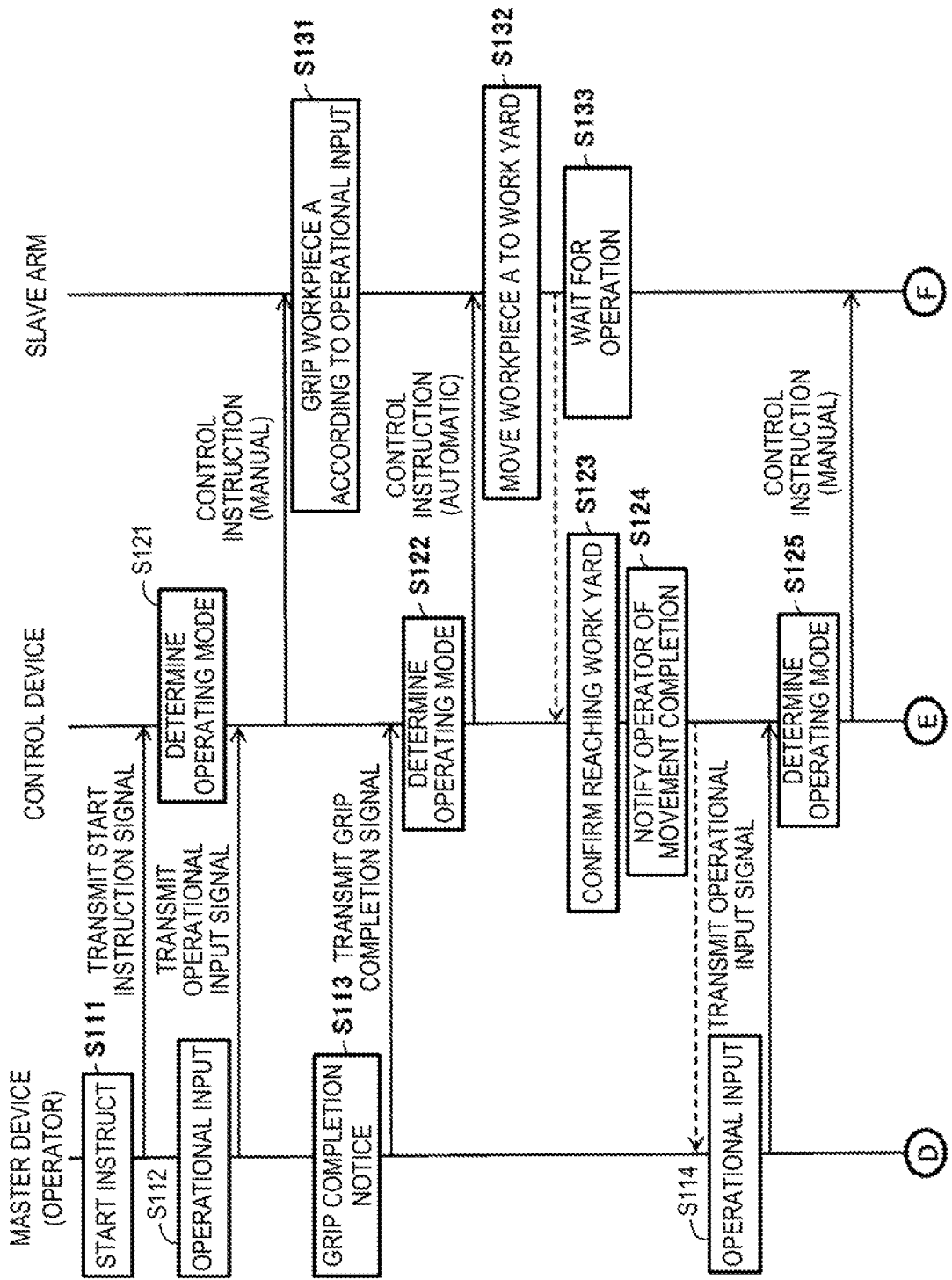
FIG. 9 is a flowchart illustrating one example of operation processing in the master device, the control device, and the slave arm, which carry out the operating sequence illustrated in FIG. 7, respectively.
Figure 10:
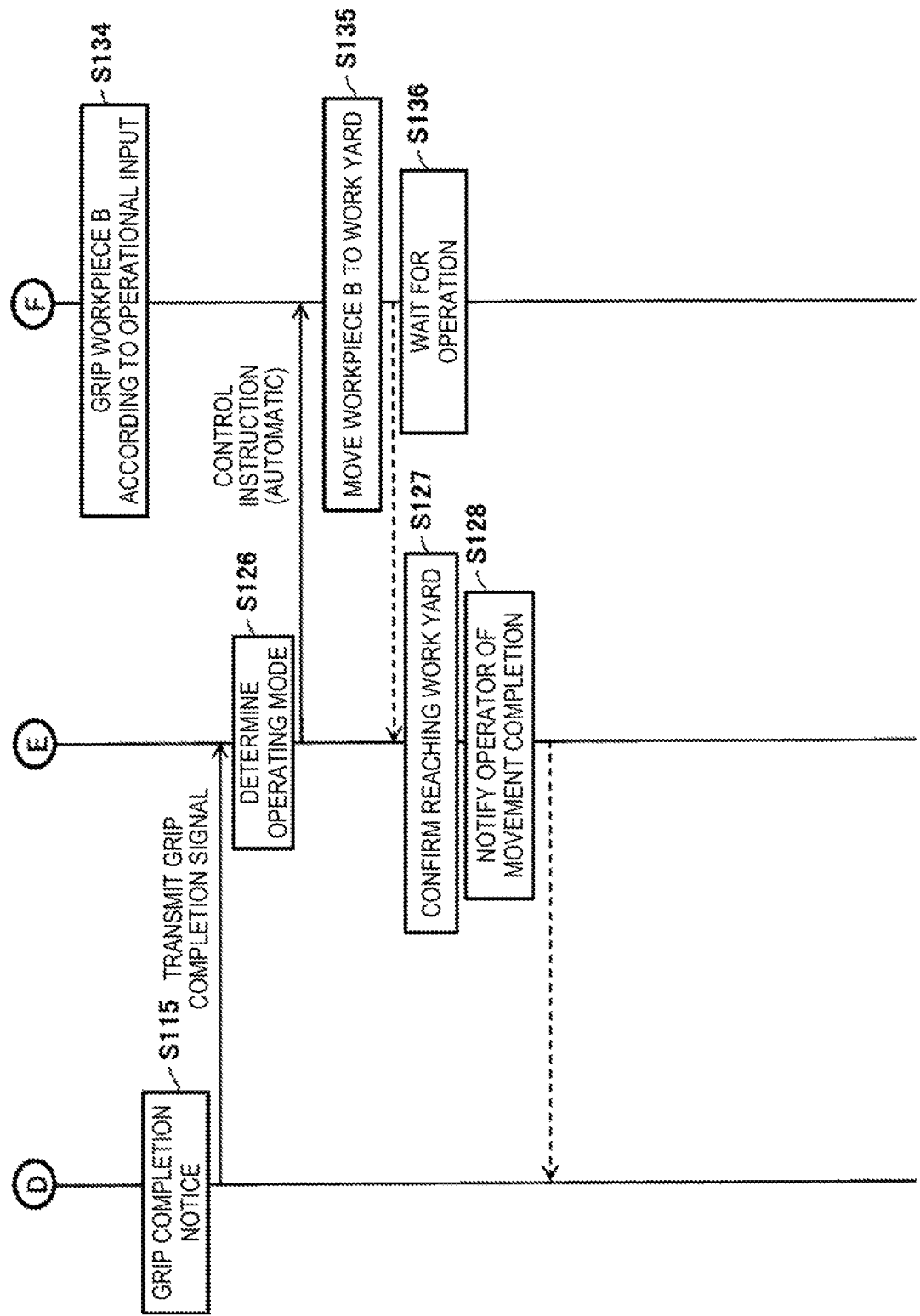
FIG. 10 is a flowchart illustrating one example of the operation processing in the master device, the control device, and the slave arm, which carry out the operating sequence illustrated in FIG. 7, respectively.

Next, with reference to FIGS. 7 to 10, the operating sequence of the robot system 100 according to Example 2 of the embodiment of the present disclosure is described. FIG. 7 is a view illustrating one example of the operating sequence of the robot system 100 according to Example 2 of the embodiment of the present disclosure. FIG. 8 is a view schematically illustrating one example of the slave arm 1 which carries out a work following the operating sequence illustrated in FIG. 7. FIGS. 9 and 10 illustrate a flowchart of one example of operation processings of the master device 9, the control device 3, and the slave arm 1 which carry out the operating sequence illustrated in FIG. 7.

In Example 2, in an environment where a plurality of workpieces are mixed within the workspace, an operating sequence of the robot system 100 using a work to grip a given workpiece and move it to a workpiece yard is described as one example. Operation orders <1> to <4> in FIG. 7 represent the operation orders in the operating sequence. Note that, in this operating sequence, the slave arm 1 grips a given workpiece out of the mixed workpieces by the manual operation according to the instruction from the operator. Meanwhile, once the workpiece is gripped, the slave arm 1 carries out the movement of the workpiece to the workpiece yard by the automatic operation.

This operating sequence related to the work comprised of the series of processings may be applicable to, for example, a moving work in which a large-sized workpiece, such as a slag or casting of which a dimension is not uniform, existing in an adverse-environmental workspace, is moved to a given position.

First, as illustrated in FIG. 9, the operator operates the master device 9 to input the start instruction (Step S111). By this input of the start instruction, the start instruction signal which instructs the start of the operating sequence is transmitted from the master device 9 to the control device 3. In the control device 3, the receiver 40 waits for the operational input signal (start instruction signal). When the start instruction signal is transmitted from the master device 9 to the control device 3, the receiver 40 receives the start instruction signal.

In the control device 3, when the receiver 40 receives the start instruction signal, the motion controller 41 determines the operating mode of the slave arm 1 (Step S121). At the operation order <1> which is the first process, the operating mode is set to the manual mode. Thus, the motion controller 41 determines that the operating mode is the manual mode. Then, the operator performs the operational input using the master arm 2 of the master device 9 (Step S112). The operational input by the operator is transmitted to the control device 3 as the operational input signal through the master arm 2 of the master device 9. The control device 3 transmits to the slave arm 1 the control instruction based on the operational input signal received from the master aim 2. Thus, the slave arm 1 operates following the operation of the master device 9. Specifically, the slave arm 1 grips the workpiece A, as illustrated in (a) of FIG. 8 according to the operational input from the master device 9 (Step S131). When the gripping of the workpiece A is completed, the operator inputs a notice of grip completion through the operation instructing part 7 of the master device 9 (Step S113). By the input of the notice of grip completion, a grip completion signal is transmitted from the master device 9 to the control device 3.

When the receiver 40 in the control device 3 receives the grip completion signal, the motion controller 41 determines the operating mode of the slave arm 1 (Step S122). In the example of the operating sequence information 51 illustrated in FIG. 7, the operating mode is set to the automatic mode in the operation order <2> which is the subsequent process. Thus, the motion controller 41 determines that the operating mode is the automatic mode, refers to the operating sequence information 51, and controls the slave arm 1 so that the slave arm 1 automatically carries out each step of the operation order <2>.

Specifically, according to the control instruction (automatic mode) from the motion controller 41, the slave arm 1 moves to the workpiece yard while gripping the workpiece A, as illustrated in (b) of FIG. 8 (Step S132). Then, the slave arm 1 places the gripped workpiece A on the workpiece yard, and waits for the operating instruction signal (Step S133).

Note that the motion controller 41 is capable of determining whether the slave arm 1 reaches the workpiece yard based on the status information acquired from the status information acquiring part 5. Note that, in FIG. 9, a dashed-line arrow extending toward the upstream of Step S123 of the control device 3 from the downstream of Step S132 of the slave arm 1 represents the acquisition of the status information by the control device 3.

Then, when the motion controller 41 confirms that the slave arm 1 reaches the workpiece yard (Step S123), it instructs the output controller 42 to report to the operator that the movement of the workpiece A is completed. The output controller 42 controls the output device 4, according to the instruction from the motion controller 41, to output information indicative of the completion of movement of the workpiece A (Step S124). Note that, in FIG. 9, a dashed-line arrow extending toward the upstream of Step S114 of the master device 9 from the downstream of Step S124 of the control device 3 represents the detection of a notice of completion of preparation by the operator.

When the completion of movement is notified by the output device 4, the operator inputs the switching instruction of the operating mode through the operation instructing part 7 of the master device 9, and performs the operational input using the master arm 2 (Step S114). As a result of these inputs, the operating mode switching signal from the operation instructing part 7 and the operational input signal from the master arm 2 are transmitted to the control device 3. In the control device 3, when the receiver 40 receives the mode switching signal, the motion controller 41 determines the operating mode of the slave arm 1 for the subsequent process (Step S125). In the example of the operating sequence information 51 illustrated in FIG. 7, the operating mode is set to the manual mode for the subsequent operation order <3>. Then, the motion controller 41 determines that the operating mode is the manual mode, and transmits to the slave arm 1 the control instruction (manual mode) based on the operational input signal received from the master arm 2.

Thus, the slave arm 1 operates following the operation of the master arm 2. Specifically, the slave arm 1 grips the workpiece B, as illustrated in (c) of FIG. 8 according to the operational input from the master arm 2 (Step S134). When the gripping of the workpiece B is completed, the operator operates the operation instructing part 7 of the master device 9 to input the notice of grip completion (Step S115). By the input of the notice of grip completion, the grip completion signal is transmitted from the master device 9 to the control device 3.

When the receiver 40 receives the grip completion signal, in the control device 3, the motion controller 41 determines the operating mode of the slave arm 1 for the subsequent process (Step S126). The motion controller 41 may be configured to perform the determination of the operating mode of the slave arm 1 by referring to the operating sequence information 51 stored in the storage device 6. Alternatively, information related to the operating mode of the slave arm 1 for the subsequent step is included in the grip completion signal transmitted from the master device 9, and the motion controller 41 may be configured to perform the determination based on this information.

In the example of the operating sequence information 51 illustrated in FIG. 7, the operating mode is set to the automatic mode in the operation order <4>. Then, the motion controller 41 determines that the operating mode is the automatic mode, and it controls so that the slave arm 1 automatically carries out each step of the operation order <4> which is the subsequent process.

Specifically, according to the control instruction (automatic mode) from the motion controller 41, the slave arm 1 moves to the workpiece yard while gripping the workpiece B, as illustrated in (d) of FIG. 8 (Step S135). Then, the slave arm 1 places the gripped workpiece A on the workpiece yard, and waits for the operating instruction signal (Step S136).

Note that the motion controller 41 may be configured to determine whether the slave arm 1 reaches the workpiece yard based on the status information acquired from the status information acquiring part 5, similar to Step S132.

Then, when the motion controller 41 confirms that the slave arm 1 reaches the workpiece yard (Step S127), it instructs the output controller 42 to notify the operator of the movement of the workpiece A having been completed. The output controller 42 controls the output device 4 to output the information indicative of the completion of movement of the workpiece B (Step S128). Note that, in FIG. 10, a dashed-line arrow extending toward the upstream of Step S127 of the control device 3 from the downstream of Step S135 of the slave arm 1 represents the acquisition of the status information by the control device 3. Moreover, a dashed-line arrow extending toward the master device 9 from the downstream of Step S128 of the control device 3 represents that the operator has detected the notice of movement completion outputted from the output device 4.

The determination of the operating mode by the motion controller 41 may be made by referring to the operating sequence information 51, using a reception by the receiver 40 of the operational input signal (the start instruction signal or the grip completion signal) transmitted from the master device 9, as a trigger. Alternatively, information indicative of the operating mode to be carried out at the subsequent process may be included in the operational input signal (the start instruction signal or the grip completion signal), and the motion controller 41 may be configured to determine the operating mode based on these signals transmitted from the master device 9. When the motion controller 41 is configured to determine the operating mode based on the signal transmitted from the master device 9, it is not necessary to include the information related to the operating mode in the operating sequence information 51 stored in the storage device 6.

EXAMPLE 3

[Continuation Permitting Determination and Operating Mode Determination]

Moreover, in Example 1 and Example 2 described above, at the process of which the operating mode is determined to be the automatic mode by the motion controller 41, the slave arm 1 is configured to operate in the automatic mode at all the steps included in this process. However, it is not limited to this configuration, but, even for the process which is determined to be the automatic mode, a determination of whether a continuation of the operation of the slave arm 1 in the automatic mode is permitted may be configured to be made according to the work status etc. of the slave arm 1, and the operating mode may be switched from the automatic mode, if needed.

For example, the slave arm 1 may be configured, when the slave arm 1 is evacuated from the assembling completed position in the automatic mode at Step S35 illustrated in FIG. 5 in Example 1, not to continuously perform the work at the subsequent step S36 illustrated in FIG. 6 in the automatic mode, but to determine whether this work at Step S36 is to be continued in the automatic mode. In other words, it may be configured so that the slave arm 1 operates in the automatic mode up to Step S35, and the determination of whether the automatic mode is to be continued is made for the steps after Step S36. Note that the timing of the continuation permitting determination of the automatic mode is not limited after Step S35 described above. As for the timing of continuation permitting determination of the automatic mode, it may be suitable to be carried out at a position before carrying out the given step, based on the content of the step carried out by the slave arm 1.

Note that, when the work performed in Example 1 and Example 2 is the painting work as described above, the process at which the slave arm 1 is scheduled to operate in the automatic mode may be, for example, a process at which the slave arm 1 is scheduled to paint the workpiece in the automatic mode. Moreover, in this process, the timing of the continuation permitting determination of the automatic mode may be, for example, a timing when the slave arm 1 paints in the automatic mode up to a given position of a painting surface. In this case, the step to be determined for the continuation permitting of the automatic mode is a step of the painting performed by the slave arm 1 to the painting surface after the given position.

Below, with reference to FIGS. 2 and 11, a configuration in which, in the process where the slave arm 1 is scheduled to operate in the automatic mode, the determination of the continuation permission of the automatic mode is made when the steps after the given step included in the process are to be carried out, is described as Example 3.

Figure 11:
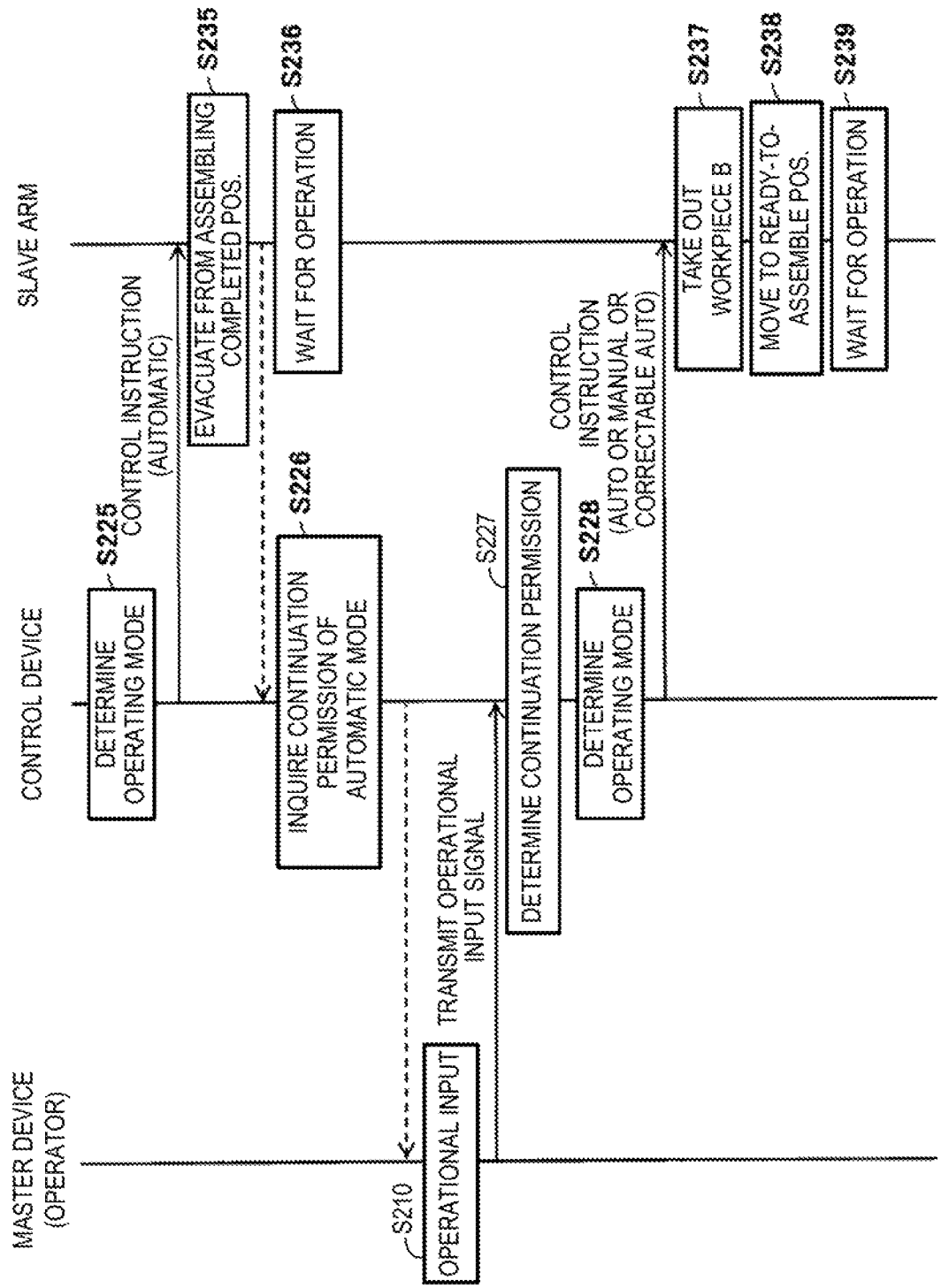
FIG. 11 is a flowchart illustrating one example of an operating sequence of the robot system according to Example 3 of the embodiment of the present disclosure.

FIG. 11 is a flowchart illustrating one example of the operating sequence of the robot system according to Example 3 of the embodiment of the present disclosure. In FIG. 11, operation of the robot system according to Example 3, using the plurality of steps included in the process of the operation order <3> illustrated in FIG. 3 is described as one example. Therefore, Steps S235, and S237 to S239 which the slave arm 1 carries out in FIG. 11 correspond to Steps S35-S38 which the slave arm 1 carries out in FIGS. 5 and 6. Moreover, Step S225 which the control device 3 carries out in FIG. 11 corresponds to Step S25 which the control device 3 carries out in FIG. 5. Thus, detailed description of these steps is omitted.

First, at Step S225, the motion controller 41 of the control device 3 determines the operating mode for the process which the slave arm 1 is scheduled to carry out next. In the example of the operating sequence information 51 illustrated in FIG. 3, the operating mode is set to the automatic mode in the operation order <3> of the subsequent process. Then, the motion controller 41 determines that the operating mode is the automatic mode. Then, the motion controller 41 controls the slave arm 1 by transmitting the control instruction (automatic mode) to the slave arm 1 so that the slave arm 1 carries out each step of the operation order <3> in the automatic mode. Then, by the control instruction from the motion controller 41, the slave arm 1 is automatically evacuated from the assembling completed position of the workpiece A (Step S235).

Next, the motion controller 41 detects that the slave arm 1 has been evacuated from the assembling completed position and has moved to the given position based on the status information acquired by the status information acquiring part 5. Then, after this detection, the motion controller 41 instructs the output controller 42 to inquire of whether the continuation of the automatic mode is permitted. According to this instruction from the motion controller 41, the output controller 42 controls the output device 4 to output the inquiry of whether the continuation of the automatic mode is permitted (Step S226). Here, the motion controller 41 suspends the operation of the slave aim 1 in the automatic mode, and makes the slave arm 1 wait for an operation (Step S236). Moreover, the receiver 40 of the control device 3 waits for the operational input signal transmitted from the master device 9.

Note that, in FIG. 11, a dashed-line arrow extending toward the upstream of Step S236 of the control device 3 from the downstream of Step S235 of the slave arm 1 represents that the control device 3 receives the status information utilized in order to confirm that the slave arm 1 has moved to the given position. Moreover, in FIG. 11, a dashed-line arrow extending toward the upstream of Step S210 of the master device 9 from the downstream of Step S226 of the control device 3 represents that the operator detects the inquiry of whether the continuation of the automatic mode is permitted.

When the inquiry of whether the continuation of the automatic mode is permitted is notified by the output device 4, the operator operates the operation instructing part 7 of the master device 9 to input instructive information related to whether the continuation of the automatic mode is permitted (Step S210). Then, the instructive information inputted through the operation instructing part 7 is transmitted to the control device 3 as the operational input signal. In the control device 3, the receiver 40 receives the operational input signal, the continuation determinator 46 determines whether the continuation of the operation of the slave arm 1 in the automatic mode is permitted (Step S227). Then, the continuation determinator 46 notifies the determination result to the motion controller 41. The motion controller 41 determines the operating mode of the slave arm 1 based on the determination result notified from the continuation determinator 46 (Step S228), and controls the slave arm 1 to operate in the determined operating mode. For example, when the determination result notified from the continuation determinator 46 is a permission of the continuation of the automatic mode, the motion controller 41 maintains the operating mode of the slave arm 1 in the automatic mode, and transmits the control instruction to the slave arm 1 to control the slave arm 1 to continuously operate in the automatic mode.

On the other hand, when the determination result notified from the continuation determinator 46 is not the permission of the continuation of the operation of the slave arm 1 in the automatic mode, the motion controller 41 determines that the operating mode of the slave arm 1 is the manual mode or the correctable automatic mode. Here, when the operating mode of the slave arm 1 is the manual mode, the motion controller 41 controls the slave arm 1 to operate in the manual mode according to the operational input signal from the master arm 2 received by the receiver 40. Alternatively, when the operating mode of the slave arm 1 is the correctable automatic mode, the motion controller 41 controls the slave arm 1 to operate while part of the operation of the slave arm 1 in the automatic mode is corrected by the operational input signal from the master arm 2.

That is, when the determination result notified from the continuation determinator 46 permits the continuation of the automatic mode, the slave arm 1 automatically takes out the workpiece B (Step S237), moves to the ready-to-assemble position (Step S238), and waits for an operation of the subsequent process (Step S239).

On the other hand, when the determination result notified from the continuation determinator 46 does not permit the continuation of the automatic mode, the slave arm 1, for example, takes out workpiece B in the manual mode or the correctable automatic mode (Step S237), moves to the ready-to-assemble position (Step S238), and waits for an operation of the subsequent process (Step S239). Alternatively, when the determination result notified from the continuation determinator 46 does not permit the continuation of the operation of the slave arm 1 in the automatic mode, the slave arm 1 may not carry out Steps S237-S239 and may maintain its operation suspended.

In Example 3, although the configuration in which the operator is inquired for whether the continuation of the automatic mode is to be permitted, and the continuation determinator 46 determines whether the automatic mode is to be continued based on the operational input signal inputted through the operation instructing part 7 of the master device 9 is described, the present disclosure is not limited to this configuration. The continuation determinator 46 may be configured to determine whether the automatic mode is to be continued based on the status information acquired by the status information acquiring part 5, without inquiring the operator of whether the continuation of the automatic mode is to be permitted.

For example, the continuation determinator 46 may be configured to determine whether the continuation of the automatic mode is to be permitted before carrying out the given step, according to a progress status of each step in the process which is carried out by the slave arm 1. More specifically, the robot system 100 may include, as the status information acquiring part 5, a measuring part which measures a completion time of each step carried out by the slave arm 1. Before carrying out the given step (the extraction of the workpiece B in the example of FIG. 11), the continuation determinator 46 may compare a time at which a step before this step (the evacuation from the assembling position in the example of FIG. 11) is completed with a scheduled completion time of the previous step (a standard time required for processing the previous step), and determine that the continuation of the automatic mode is not permitted when the difference is more than a given range. On the contrary, the continuation determinator 46 may be configured to compare the time at which the evacuation from the assembling position is completed with the scheduled completion time of the evacuation from the assembling position (the standard time required for completing the evacuation), and permit the continuation of the automatic mode when the difference falls within the given range. When configured in this way, Step S226 which the control device 3 carries out and Step S210 which the master device 9 carries out in FIG. 11 may be omitted.

Alternatively, for example, when a sensor which grasps the position of the slave arm 1 in the workspace is provided as the status information acquiring part 5, the continuation determinator 46 may be configured to determine whether the continuation of the automatic mode is to be permitted based on the result detected by the sensor. More specifically, based on the detection result of the sensor described above, it is determined at Step S235 whether the slave arm 1 is evacuated into a given range. Then, when determined that the slave arm 1 is not evacuated into the given range, the continuation determinator 46 does not permit the continuation of the automatic mode. On the other hand, when determined that the slave arm 1 exists within the given range, the continuation determinator 46 may be configured to permit the continuation of the automatic mode.

EXAMPLE 4

[Configuration of Inquiring Operating Mode]

Figure 12:
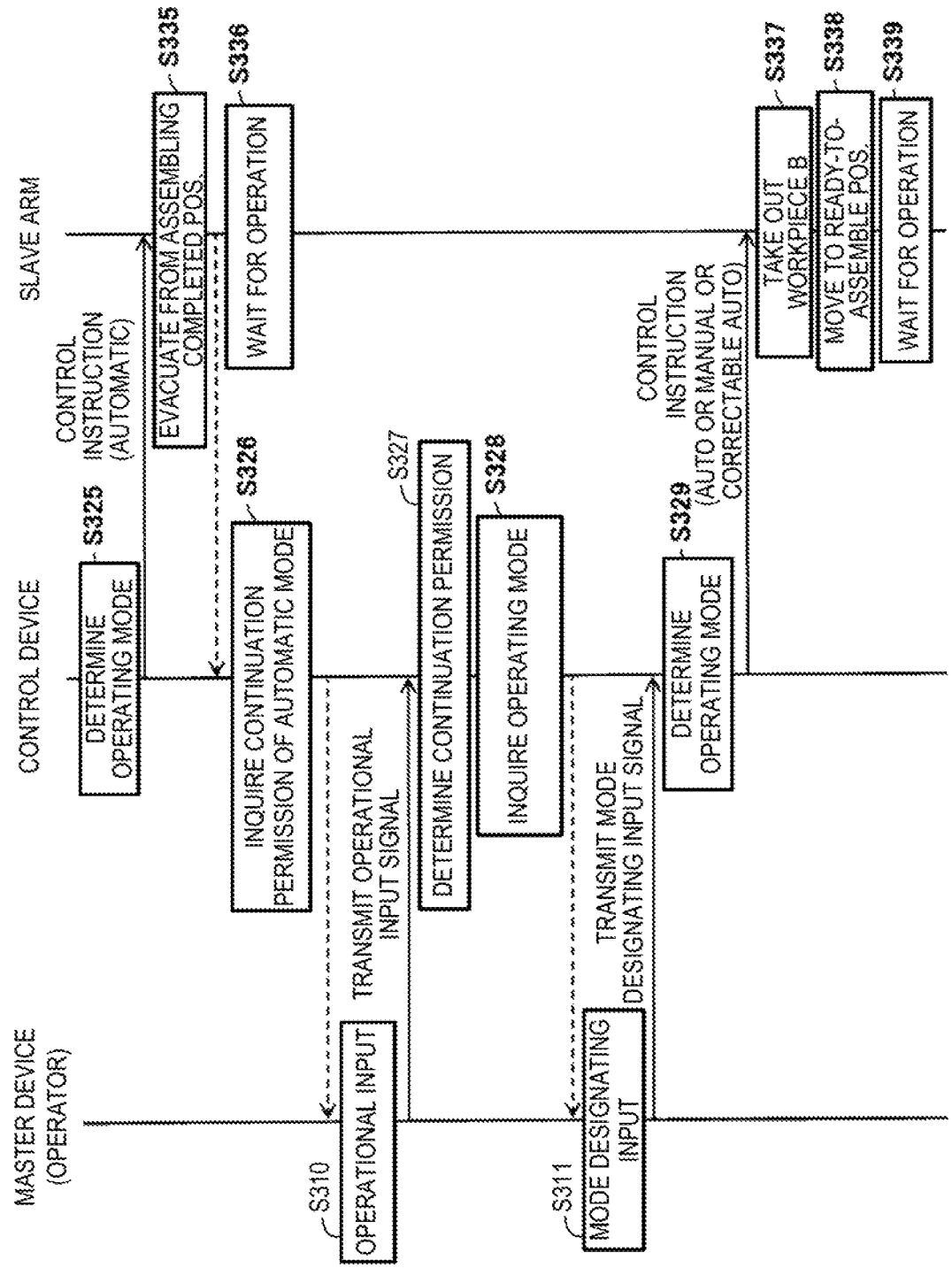
FIG. 12 is a flowchart illustrating one example of an operating sequence of the robot system according to Example 4 of the embodiment of the present disclosure.

In the robot system 100 according to Example 3, the control device 3 is configured to inquire the operator of whether the continuation of the automatic mode is to be permitted at Step S226 illustrated in FIG. 11, and determine the operating mode at Step S227. In the robot system 100 according to Example 4, as illustrated in FIG. 12, it is configured to be able to inquire the operator of a new operating mode when the continuation of the automatic mode is not permitted in the operating sequence of the robot system 100 according to Example 3 illustrated in FIG. 11. Then, the motion controller 41 determines the operating mode of the slave arm 1 based on the input from the operator according to the inquiry, and controls the slave arm 1 to operate in the determined operating mode. FIG. 12 is a flowchart illustrating one example of the operating sequence of the robot system 100 according to Example 4 of the embodiment of the present disclosure.

The operating sequence of the robot system 100 according to Example 4 as illustrated in FIG. 12 is similar to the operating sequence of the robot system 100 according to Example 3 illustrated in FIG. 11, except that a step at which the control device 3 inquires the operating mode (Step S328), and a step at which the master device 9 (operator) performs a mode designating input according to the inquiry (Step S311) are added. Thus, in FIG. 12, only Step S328 in the operation flow of the control device 3 and Step S311 in the operation flow of the master device 9 are described, and description of other steps is omitted.

When the continuation determinator 46 of the control device 3 determines at Step S327 that the continuation of the automatic mode is not permitted, the motion controller 41 inquires the operator for the operating mode in which the slave arm 1 operates in the subsequent step (Step S328). More specifically, the motion controller 41 instructs the output controller 42 to inquire the operating mode of the slave arm 1. According to the instruction from the motion controller 41, the output controller 42 controls the output device 4 to output the inquiry of the operating mode (operating mode inquiry information) (Step S328). Here, the receiver 40 of the control device 3 waits for the operational input signal (mode designating input signal) transmitted from the master device 9.

Note that, in FIG. 12, a dashed-line arrow extending toward the upstream of Step S311 of the master device 9 from the downstream of Step S328 of the control device 3 represents that the operator detects the inquiry of the operating mode.

When the inquiry of the operating mode is notified by the output device 4, the operator performs the mode designating input through the operation instructing part 7 of the master device 9 (Step S311). The mode designating input by the operation instructing part 7 is transmitted to the control device 3 as the mode designating input signal. In the control device 3, when the receiver 40 receives the mode designating input signal, the motion controller 41 determines the operating mode of the slave arm 1 (Step S329). Then, the motion controller 41 controls the slave arm 1 to operate in the determined operating mode.

Note that, as for the mode of the inquiry of the operating mode by the output device 4, it is desirable to be suitably selected according to the operator's work environment and the type of work which the operator carries out. For example, when the output device 4 is the speaker, the inquiry of the operating mode may be notified to the operator by sound. When the output device 4 is the light source, the operating mode may be inquired to the operator by light. Alternatively, when the output device 4 is the oscillation generating device, the operating mode may be inquired to the operator by vibration.

From the above description, it is apparent for a person skilled in the art that many improvements and other embodiments of the present disclosure are possible. Therefore, the above description is to be interpreted only as illustration, and it is provided in order to teach a person skilled in the art the best mode in which implements the present disclosure. Details of the structures and/or functions of the present disclosure may be substantially changed without departing from the spirit of the present disclosure.

INDUSTRIAL APPLICABILITY

As described above, the robot system 100 according to the present disclosure is widely applicable to the system having the automatic mode, the manual mode, and the correctable automatic mode as the operating mode of the slave arm.

DESCRIPTION OF REFERENCE CHARACTERS

1 Slave Arm
2 Master Arm
3 Control Device
4 Output Device
5 Status Information Acquiring Part
6 Storage Device
7 Operation Instructing Part
9 Master Device
10 Slave Robot
40 Receiver
41 Motion Controller
42 Output Controller
46 Continuation Determinator
51 Operating Sequence Information
100 Robot System

What is claimed is:

1. A robot system, comprising:
   a master device configured to receive an operating instruction from an operator;
   a slave arm configured to perform, in a process containing a plurality of steps, processing of the steps;
   a storage device configured to store operating sequence information that defines the processing carried out by the slave arm; and
   a control device configured to control operation of the slave arm, the control device including:
      a receiver configured to receive an input signal;
      a motion controller configured to determine whether an operating mode of the slave arm is to be an automatic mode in which the slave arm is operated based on the operating sequence information, or a manual mode in which the slave arm is operated based on the operating instruction inputted through the master device, or a correctable automatic mode in which the operation of the slave arm under operation in the automatic mode is corrected based on the operating instruction inputted through the master device, and control the operation of the slave arm in the determined operating mode; and
      a continuation determinator configured to determine whether a continuation of the automatic mode is permitted,
   wherein, in a process at which the slave arm is scheduled to operate in the automatic mode, after the motion controller suspends the operation of the slave arm in the automatic mode at a given step of the process, the continuation determinator determines whether the continuation of the automatic mode is permitted based on the input signal received by the receiver when the operation is suspended.

2. The robot system of claim 1, comprising an output device configured to output information to be notified to the operator,
   wherein, after the motion controller suspends the operation of the slave arm in the automatic mode at the given step, the output device outputs an inquiry of whether the continuation of the automatic mode is permitted as the information to be notified to the operator, and
   the continuation determinator determines whether the continuation of the operation of the slave arm in the automatic mode is permitted based on the input signal received by the receiver according to the output of the inquiry by the output device.

3. The robot system of claim 2, wherein the master device includes a master arm configured to input the operating instruction into the slave arm, and a switch or a mobile terminal configured to input the input signal.

4. The robot system of claim 1, further comprising a status information acquiring part configured to acquire status information indicative of a status of the slave arm in a workspace,
   wherein the receiver receives the status information acquired by the status information acquiring part as the input signal, and wherein, after the motion controller suspends the operation of the slave arm in the automatic mode at the given step, the continuation determinator determines whether the continuation of the operation of the slave arm in the automatic mode is permitted based on the status information received by the receiver.

5. The robot system of claim 2, wherein, when the continuation determinator determines that the continuation of the operation of the slave arm in the automatic mode is not permitted, the output device outputs the inquiry of the operating mode of the slave arm as the information to be notified to the operator, and wherein the motion controller determines the operating mode of the slave arm at and after a subsequent step of the given step based on the input signal received by the receiver according to the output of the inquiry of the operating mode by the output device.

6. The robot system of claim 5, wherein the output device outputs the inquiry of the operating mode of the slave arm by sound, light, or vibration.

* * * * *